(12) United States Patent
Bezwada

(10) Patent No.: US 7,902,319 B2
(45) Date of Patent: Mar. 8, 2011

(54) UNSYMMETRICAL AROMATIC ETHER DIACIDS AND ABSORBABLE POLYMERS THEREFROM

(75) Inventor: Rao S. Bezwada, Hillsborough, NJ (US)

(73) Assignee: Bezwada Biomedical, LLC, Hillsborough, NJ (US)

(*) Notice: Subject to any disclaimer, the term of this patent is extended or adjusted under 35 U.S.C. 154(b) by 0 days.

(21) Appl. No.: 12/684,443

(22) Filed: Jan. 8, 2010

(65) Prior Publication Data

US 2010/0113592 A1 May 6, 2010

Related U.S. Application Data

(60) Division of application No. 11/679,191, filed on Feb. 27, 2007, now Pat. No. 7,671,168, which is a continuation-in-part of application No. PCT/US2006/060002, filed on Oct. 16, 2006.

(60) Provisional application No. 60/728,823, filed on Oct. 21, 2005.

(51) Int. Cl.
*C08G 63/02* (2006.01)
*A61F 2/00* (2006.01)

(52) U.S. Cl. .......................... 528/272; 528/425; 424/426

(58) Field of Classification Search .................. 528/272, 528/425; 424/426
See application file for complete search history.

(56) References Cited

U.S. PATENT DOCUMENTS

| | | |
|---|---|---|
| 3,044,942 A | 7/1962 | Baptist |
| 3,297,033 A | 1/1967 | Schmitt |
| 3,371,069 A | 2/1968 | Miyamae |
| 3,531,561 A | 9/1970 | Trehu |
| 3,636,956 A | 1/1972 | Schneider |
| 3,773,737 A | 11/1973 | Goodman |
| 4,052,988 A | 10/1977 | Doddi |
| 4,130,639 A | 12/1978 | Shalaby |
| 4,532,928 A | 8/1985 | Bezwada |
| 4,605,730 A | 8/1986 | Shalaby |
| 4,653,497 A | 3/1987 | Bezwada |
| 4,689,424 A | 8/1987 | Shalaby |
| 4,829,099 A | 5/1989 | Fuller |
| 4,886,870 A | 12/1989 | Langer |
| 4,938,949 A | 7/1990 | Borch |
| 5,082,925 A | 1/1992 | Shalaby |
| 5,099,060 A | 3/1992 | Kohn |
| 5,264,540 A | 11/1993 | Cooper |
| 5,521,431 A | 5/1996 | Tahara |
| 5,759,830 A | 6/1998 | Vacanti |
| 5,801,033 A | 9/1998 | Hubbell |
| 5,834,274 A | 11/1998 | Hubbell |
| 5,834,513 A | 11/1998 | Ptchelintsev |
| 5,843,743 A | 12/1998 | Hubbell |
| 5,895,150 A | 4/1999 | Kowski |
| 5,902,599 A | 5/1999 | Anseth |
| 5,932,229 A | 8/1999 | Ptchelintsev |
| 5,942,252 A | 8/1999 | Tice |
| 5,951,997 A | 9/1999 | Bezwada |
| 6,468,519 B1 | 10/2002 | Uhrich |
| 6,689,350 B2 | 2/2004 | Uhrich |
| 6,773,721 B1 | 8/2004 | Wong |
| 6,861,068 B2 | 3/2005 | Ng |
| 6,869,615 B2 | 3/2005 | Chen |
| 6,887,974 B2 | 5/2005 | Pathak |
| 6,890,561 B1 | 5/2005 | Blatt |
| 2002/0169275 A1 | 11/2002 | Matsuda |
| 2003/0158598 A1 | 8/2003 | Ashton |
| 2003/0216307 A1 | 11/2003 | Kohn |
| 2003/0232091 A1 | 12/2003 | Shefer |
| 2004/0096476 A1 | 5/2004 | Uhrich |
| 2004/0117007 A1 | 6/2004 | Whitbourne |
| 2005/0048121 A1* | 3/2005 | East et al. ..................... 424/486 |
| 2005/0074493 A1 | 4/2005 | Mehta |
| 2005/0095300 A1 | 5/2005 | Wynn |
| 2005/0112171 A1 | 5/2005 | Tang |
| 2005/0152958 A1 | 7/2005 | Cordes |
| 2005/0238689 A1 | 10/2005 | Carpenter |
| 2006/0013851 A1 | 1/2006 | Giroux |
| 2010/0170927 A1 | 7/2010 | Bezwada |

FOREIGN PATENT DOCUMENTS

| | | |
|---|---|---|
| WO | WO 97/39738 | 10/1997 |
| WO | WO 98/36013 | 8/1998 |
| WO | WO 99/12990 | 3/1999 |
| WO | WO 99/29885 | 6/1999 |
| WO | WO 01/41753 | 6/2001 |
| WO | WO 02/09767 | 2/2002 |
| WO | WO 02/09768 | 2/2002 |
| WO | WO 2004/008101 | 1/2004 |
| WO | WO 2006/052790 | 5/2006 |
| WO | WO 2007/030464 | 3/2007 |
| WO | WO 2007/030538 | 3/2007 |

OTHER PUBLICATIONS

J. Org. Chem, 1959, 24, 523-526.
Gutowska et al, J. Biomater, Res., 29, 811-21 (1995).
Hoffman, J. Controlled Release, 6, 297-305 (1987).
Mikos et al, Biomaterials, 14, 323-329 (1993).
Shugens et al, J. Biomed. Mater. Res., 30, 449-462 (1996).
Bulletin of the Material Research Society, Special Issue on Tissue Engineering (Guest Editor: Joachim Kohn), 21(11), 22-26 (1996).
Remington's Pharmaceutical Sciences, $18^{th}$ ed., Mack Publishing Company, Eason, PA, 1990, p. 1445.
Shahidi, Ferriodoon and Marian Naczk, Phenolics in Food and Nutriceuticals, Boca Raton, FL :CRC Press, 2003.
Kleemann, A. et al, Pharmaceutical Substances, $4^{th}$ edition, Thieme (2000).
Phenolic Compounds in Food and Their Effects on Health II; Antioxidants and Cancer Prevention, ACS Symposium Series No. 507, Washington, DC: ACS, 1992.

(Continued)

*Primary Examiner* — Duc Truong
(74) *Attorney, Agent, or Firm* — Feldman Gale, P.A.; Walter C. Frank

(57) ABSTRACT

The present invention relates to compounds and compositions of formula I, which are unsymmetrical aromatic ether diacids, and polymers formed from the same.

$$[R'—(Y)_p—O]_q—Ar—[O—(X)_r—R']_s \qquad I$$

The compounds are expected to be useful in a variety of medical and/or cosmetics applications. Polymers formed from the functionalized unsymmetrical aromatic ether diacids are expected to have controllable degradation profiles, enabling them to release an active component over a desired time range.

34 Claims, No Drawings

OTHER PUBLICATIONS

Food Phytochemicals for Cancer Prevention I, ACS Symposium Series N. 546, Washington, DC: ACS, 1994.

ROMPP Encyclopedia Natural Products, New York: Thieme, 2000.

Helder, et al, J. Biomed. Mater. Res., (24), 1005-1020 (1990).

Barrera, et al, Macromolecules, (28), 425-432 (1995).

Langer, R., Science 249: 1527-1533 (1990).

van Dijk-Wolthuis, W.N.W.; Hoogeboom, J.; van Steenbergen, M.; Tsang, S.; and Hennick, W., "Degradation and Release Behavior of Dextran-Based Hydrogels", Macromolecules, 30; (1997) 4639-4645.

van Dijk-Wolthuis, W.N.E.; Tsang, S.; Kettenes-van den Bosch, J.; and Hennick, W. "A new class of polymerizable dextrans with hydrolysable groups: hydroxyethyl methacrylated dextran with and without oligolactate spacer", Polymer, 39 (25); (1997) 6235-6242.

Kurisawa et al, Macromol. Chem. Phys. 199, 705-709 (1998).

Heller, J.; Helwing, R.F.; Baker, R.W.; and Tuttle, M.E. "Controlled release of water-soluble macromolecules from bioerodible hydrogels" Biomaterials, 4; (1983) 262-266.

Brondsted (Brondsted, H.; and Kopccek, J. "Hydrogels for site-specific oral drug deliver: synthesis and characterization" Biomaterials, 12; (1991) 584-592.

Ulbrich, K.; Subr, V.; Seymour, L.W.; and Duncan, R. "Novel biodegradable hydrogels prepared using the divinylic crosslinking agent N, O-dimethacryloylhydroxylamine 1. Synthesis and characterization of rates of gel degradation, and rate of release of model drugs, in vitro and in vivo" Journal of Controlled Release, 24; (1993) 181-190.

Trenor, "Synthesis and characterization of tailored photoactive macromolecules", Apr. 16, 2004, Abstract p. 1, 5-7.

* cited by examiner

UNSYMMETRICAL AROMATIC ETHER DIACIDS AND ABSORBABLE POLYMERS THEREFROM

CROSS-REFERENCE TO RELATED APPLICATIONS

The present application is a divisional application under 35 U.S.C. §121 of U.S. patent application Ser. No. 11/679,191, filed Feb. 27, 2007, now U.S. Pat. No. 7,671,168 which claims benefit of priority under 35 U.S.C. §120 as a Continuation-In Part of International Application PCT/US2006/060002, which designates the U.S., was filed 16 Oct. 2006, and which claims priority to U.S. Provisional Patent Application No. 60/728,823, filed 21 Oct. 2005. All of these applications are hereby incorporated herein by reference in their entireties.

FIELD OF THE INVENTION

The present invention relates to the discovery of unsymmetrical aromatic ether diacids and absorbable polymers derived therefrom, which can have controllable degradation profiles.

BACKGROUND OF THE INVENTION

There are a vast number of known phenolic compounds or phenolics (e.g., flavonoids) with a variety of known beneficial uses. Phenolic and polyphenolic compounds are found widely in nature: in cereals, legumes, nuts, oilseeds, plant oils, fruits, vegetables, tea, coffee, cocoa, beer, wine, herbal products, such as Echinacea, ginseng, gingko biloba, St. John's wort, valerian, hawthorne, ginger, licorice, milk thistle, goldenseal, devil's claw, black cohosh, saw palmetto, and kava kava, for example. These substances are essential for growth and reproduction of plants and serve as antifeedants and antipathogens, among other purposes. Phenolic compounds can also aid in the maintenance of food, fresh flavor, taste, color, and prevention of oxidation deterioration. Many phenolic compounds are attracting the attention of food and medical scientists because of their antioxidative, anti-inflammatory, antimutagenic, and anticarcinogenic properties, and their capacity to modulate key cellular enzyme function. Phenolics pigment plant products and function as antibiotics, natural pesticides, signal substances for the establishment of symbiosis with rhizobia, attractants for pollinators, protective agents against ultraviolet light, insulating materials to make cell walls impermeable to gas and water, and as structural materials to give plants stability. The members of this class have many valuable uses in the fields of nutrition, nutraceuticals, pharmaceuticals, medicine, agriculture, chemistry, and in other fields of technology.

Reactions of phenolics with bioabsorbable polymers have been reported in Shalaby U.S. Pat. No. 5,082,925 and Matsuda US 20020169275. Reactions of bioactive compounds with bioabsorbable polymers have been reported, for example, in Uhrich U.S. Pat. No. 6,468,519; Uhrich U.S. Pat. No. 6,689,350; and, Kohn US20030216307.

Various types of controlled release technologies, some of which may be suitable for use with phenolic compounds have been reported in the literature. Examples include Blatt U.S. Pat. No. 6,890,561; Chen U.S. Pat. No. 6,869,615; Cordes US 2005/0152958; Wynn U.S. Pat. No. 2005/0095300; Mehta U.S. Pat. No. 2005/0074493; Ng U.S. Pat. No. 6,861,068; Wong U.S. Pat. No. 6,773,721; Whitborne U.S. Pat. No. 2004/0117007; and, Shefer U.S. Pat. No. 2003/0232091.

Uses of bioabsorbable polymers in the biomedical field have been reported, for example, in the following patents and publication: Shalaby U.S. Pat. No. 4,130,639; Bezwada U.S. Pat. No. 4,532,928; Langer U.S. Pat. No. 4,886,870; Shalaby U.S. Pat. No. 4,605,730; Bezwada U.S. Pat. No. 4,653,497; Shalaby U.S. Pat. No. 4,689,424; Vacanti U.S. Pat. No. 5,759,830; Jamiolkowski U.S. Pat. No. 5,895,150; Bezwada U.S. Pat. No. 5,951,997; and, Yiewen U.S. Pat. No. 2005/0112171.

Unfortunately, phenolic compounds generally can be difficult to dissolve in water or the human body and can also be very difficult to polymerize in the phenolic state. Due to the availability and numerous uses of phenolics, it is desirable to enhance their native value by, for example, providing compounds or combinations of compounds with a specific controlled degradation profile or range enabling controlled release of the phenolic over an extended, controllable time range. The present invention is aimed at overcoming these drawbacks.

SUMMARY OF INVENTION

The present invention provides novel unsymmetrical aromatic ether diacids, which are hydrolysable and can be useful for medical applications (e.g., drug delivery and solvent for dissolving drugs).

The present invention also provides novel, absorbable polymers and co-polymers (e.g., polyesters, polyamides, polyester amides, and polyanhydrides) derived from unsymmetrical aromatic ether diacids. These polymers are expected to have controllable degradation profiles.

The present invention also provides novel medical devices comprising unsymmetrical aromatic ether diacids or polymers derived therefrom.

Other features of the present invention will be pointed out in the following description and claims.

DETAILED DESCRIPTION OF THE PRESENT INVENTION

The present invention provides novel unsymmetrical aromatic ether diacids and absorbable polymers derived therefrom. The present invention is designed to extend the usefulness of diphenol compounds while retaining their inherent biological properties. The diphenol compounds are unsymmetrically functionalized with safe and biocompatible molecules (e.g., glycolic acid, lactic acid, caprolactone, and dioxanone) to form unsymmetrical aromatic ether diacids. The novel unsymmetrical aromatic ether diacids of the present invention are expected to have controllable hydrolysis profiles, improved bioavailability, improved efficacy, and enhanced functionality.

It is noted that unsymmetrical aromatic ether diacids and polymers therefrom will have less crystallinity compare to the corresponding symmetrical diacids. When lower crystallinity or liquid monomers and polymers are required, unsymmetrical molecules can provide desirable properties. Liquid absorbable polymers with controllable hydrolysis profile can be very useful for control release of injectable drugs. One of the benefits of the present invention is the capability of designing a desired hydrolysis profile. Since each functionalized acid has a different hydrolysis profile (glycolic acid vs lactic acid vs caprolactone), when the diphenolic compounds are functionalized with different ether acids, a controllable hydrolysis profile can be designed for each molecule based on the ether diacids that are used.

Some of the unsymmetrical aromatic ether diacids of the present invention can be used as monomers from which polymers can be made that are useful for medical applications. For example, a diphenol compound can be functionalized to form an unsymmetrical aromatic ether diacid that can then be polymerized to form an absorbable polymer (e.g., polyesters, polyamides, polyester amides, and polyanhydrides). It can be advantageous for the monomers that are to be polymerized to have more than the two active diacid sites for polymerization (e.g., 3 active sites). These active sites include the two carboxylic acid groups of the diacids as well as optional additional active sites (e.g., hydroxyl, amino, and carboxylic acid). Examples of these combinations include (a) two diacids, (b) two diacids and a hydroxyl group, (c) two diacids and an amino group, and (d) three diacids. The unsymmetrical aromatic ether diacids can be polymerized to form polyanhydrides or copolymerized with selected difunctional compounds (e.g., dialcohols, amino-alcohols, and diamines) to form absorbable polymers. The copolymers of the present invention that comprise unreacted active sites (e.g., free hydroxyl, amine, or acid groups) can be further reacted/polymerized to form additional useful polymers of the present invention. These further reactions include capping the unreacted active site with a functional group (e.g., etherify an alcohol, esterify an acid, alkylate an amine) and polymerization with an appropriate monomer to form crosslinked polymers.

The definitions and examples provided in this application are not intended to be limiting, unless specifically stated.

Unsymmetrical aromatic ether diacids, sometimes called functionlized diphenols, are compounds derived from diphenol substances, wherein at least two hydroxyl groups from the original diphenol are functionalized to be different from each other. This is achieved by functionalizing the hydroxyl groups with different acid moieties (or different numbers of the same acid moiety).

Diphenols are compounds that have at least one aromatic ring (e.g., phenyl or naphthyl) that is substituted with at least two hydroxyl groups (e.g., 2, 3, 4, 5, and 6)(e.g., dihydroxy-phenyl, trihydroxy-phenyl, dihydroxy-naphthyl, and trihydroxy-naphthyl). When more than one aromatic ring is present (e.g., naphthyl or anthracenyl), the hydroxyl groups can be present on different rings. Diphenols are typically bioactive substances occurring widely in food plants that are eaten regularly by substantial numbers of animals and people and have been found to be safe compounds.

Phenolic residue (or diphenolic residue) means the portion of the phenol (or diphenol) compound remaining after removing a hydrogen from at least one hydroxyl group.

Polymers of the present invention can be formed solely from the present unsymmetrical aromatic ether diacids to form polyanhydrides. If the diacids are substituted by an additional active site capable of reacting with one of the carboxylic acids of the unsymmetrical aromatic ether diacids (e.g., an amino group or a third hydroxyl group that has not been functionalized), then other types of polymers can be formed by polymerization of the unsymmetrical aromatic ether diacids (e.g., polyesters and polyamides). Polymers can also be copolymers formed from at least one of the unsymmetrical aromatic ether diacids of the present invention and at least one type of difunctional compound (as described herein). Thus polymers are intended to include both polymers (one type of monomer) and copolymers (e.g., more than one type of unsymmetrical aromatic ether diacid monomer, or an unsymmetrical aromatic ether diacid and a difunctional compound).

Ar, as used herein, is an aromatic moiety that typically has 1, 2, 3, 4, 5, or 6 aromatic rings (e.g., phenyl) and bear one or more hydroxyl substituents (e.g., 1, 2, 3, 4, 5, 6, 7, 8, 9, 10, 11, 12, 13, 4, 15, 16, 17, 18, 19, 20, 21, 22, 23, 24, and 25) on at least one of the aromatic rings. Additional examples of the number of aromatic groups present in the diphenol include (a) 1, 2, and 3 and (b) 1 and 2. Additional examples of the number of hydroxyl groups present on the diphenol include (a) 2, 3, 4, and 5 and (b) 2 and 3. From two to all of the hydroxyl groups present on the diphenol compound may be functionalized, provided that at least two of the functionalized hydroxyl groups are different (i.e., unsymmetrical).

The aromatic rings of the Ar group can be fused together (e.g., naphthyl), bonded together (e.g., bi-phenyl), or linked together via a linking group. Typical linking groups include, O, S(O)$_{0-2}$, NH (or a substituted amine, e.g., substituted with a C$_{1-6}$ alkyl, phenyl, or benzyl), C$_{1-6}$ alkylene, or a C$_{1-6}$ alkylene wherein one or two of the alkylene carbon atoms is/are replaced by one or two of the previously noted heteroatoms. The aromatic rings of the Ar group can also be fused to heteroaryl rings and/or non-aromatic rings. Examples of heteroaryl rings include 5-6 membered rings consisting of carbon atoms and 1-4 heteroatoms selected from O, N, and S(O)$_{0-2}$. Examples of non-aromatic rings include 5-6 membered carbocyclic or heterocyclic rings consisting of carbon atoms and 0-3 heteroatoms selected from O, N, and S(O)$_{0-2}$. The non-aromatic rings can consist of 0-2 ring double bonds as well as 0-2 carbonyl groups attached to the ring. Examples of non-aromatic rings include pyran and pyranone. The non-aromatic rings can also be substituted by 1-2 carbonyl groups, in addition to other substituents defined elsewhere. When more than one aromatic ring is present (e.g., two phenyl rings), then they can be separated by a heteroaryl or non-aromatic ring as described above. For example, a phenyl ring can be bound to a chromene-2-one.

Examples of Ar include the following:

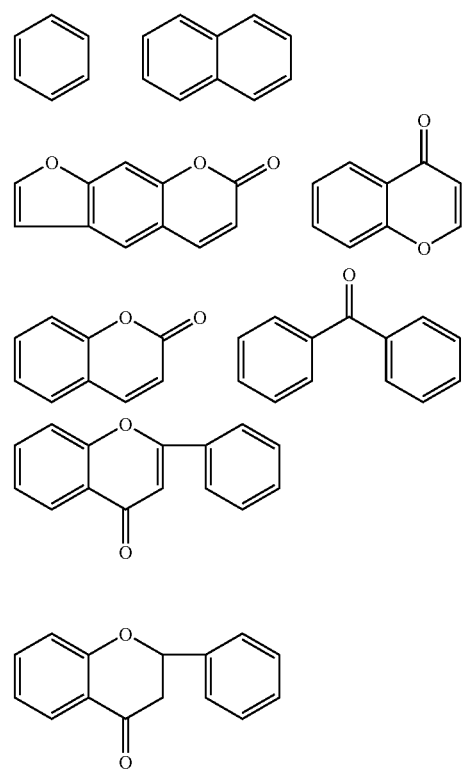

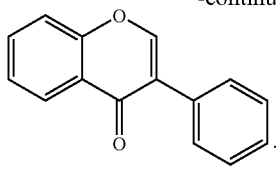

Each of the phenyl rings shown in the above examples is substituted with 0, 1, or 2 OH groups, wherein at least two OH groups are present.

The Ar group of the present invention is substituted or unsubstituted. They can be substituted with (a) 1, 2, 3, 4, 5 or 6 R groups; (b) 1, 2, or 3 R groups; (c) 1 or 2 R; or (d) 1 R.

Examples of substituent R include H, =O, O-glycosides, —$(CH_2)_{0-2}$—$OR^a$, —$(CH_2)_{0-2}$—$C_6H_5$, —$(CH_2)_{0-2}$—CHO, Cl, F, Br, I, —$(CH_2)_{0-2}$—OC(O)—$R^a$, —$(CH_2)_{0-2}$—$CO_2$—$R^a$, —$(C(CH_3))_{0-2}$—$CO_2$—$R^a$, —$(CH_2)_{0-2}$—$CO_2$—$(CH_2)_{1-2}$—$CO_2$—$R^a$, —$(C(CH_3))_{0-2}$—$CO_2$—$(CH_2)_{1-2}$—$CO_2$—$R^a$, —$(CH_2)_{0-2}$—CO—$R^a$, —$O(CH_2)_{0-2}$—$C_6H_5$, —$O(CH_2)_{1-2}$—$CO_2$—$R^a$, —$O(C(CH_3))_{1-2}$—$CO_2$—$R^a$, —$O(CH_2)_{1-2}$—CO—$R^a$, —$CO_2(CH_2)_{1-2}$—$CO_2$—$R^a$, —$CO_2(C(CH_3))_{1-2}$—$CO_2$—$R^a$, —$(CH_2)_{0-2}$—$NO_2$, —$(CH_2)_{0-2}$—$NR^aR^a$, —$(CH_2)_{0-2}$—$NR^aCOR^a$, —$(CH_2)_{0-2}$—$NR^aC(O)(CH_2)_{1-2}OR^a$, —$C_6H_5$, —$C_6H_5OR^a$, and —$C_6H_5$—CH=$CHCO_2R^a$.

Examples of $R^a$ include H and $C_{1-6}$ alkyl;

As described herein, the unsymmetrical aromatic ether diacids and polymers of the present invention are expected to be useful in medical applications/medical devices. Medical application/medical devices, as used herein, encompass medical and biomedical applications and include all types of applications involved in the practice of medicine that would benefit from a material that decomposes harmlessly within a known period of time. Examples include medical and surgical devices, which include drug delivery systems (e.g., a site-specific or systemic drug delivery systems or matrices), tissue engineering (e.g., tissue scaffold), stent coatings, stents, porous devices, implantable medical devices, molded articles (e.g., vascular grafts, stents, bone plates, sutures, implantable sensors, and barriers for surgical adhesion prevention), wound closure devices (e.g., surgical clips, staples, and sutures), coatings (e.g., for endoscopic instruments, sutures, stents, and needles), fibers or filaments (which may be attached to surgical needles or fabricated into materials including sutures or ligatures, multifilament yarn, sponges, gauze, tubes, and sheets for typing up and supporting damaged surface abrasions), rods, films (e.g., adhesion prevention barriers), knitted products, foodstuffs, nutritional supplements, nutraceuticals, cosmetics, pharmaceuticals, biodegradable chewing gums, flavors, enhanced drugs, drug intermediates, cancer preventing agents, antioxidants, controlled release preparations, and solvents for drugs. Examples of knitted products, woven or non-woven, and molded products include: burn dressings; hernia patches; medicated dressings; fascial substitutes; gauze, fabric, sheet, felt, or sponge for liver hemostasis; gauze bandages; arterial graft or substitutes; bandages for skin surfaces; suture knot clip; orthopedic pins, clamps, screws, and plates; clips (e.g., for vena cava); staples; hooks, buttons, and snaps; bone substitutes (e.g., mandible prosthesis); intrauterine devices (e.g., spermicidal devices); draining or testing tubes or capillaries; surgical instruments; vascular implants or supports; vertebral discs; extracorporeal tubing for kidney and heart-lung machines; and, artificial skin.

The present invention provides novel unsymmetrical aromatic ether diacids of formula I or a pharmaceutically acceptable salt thereof:

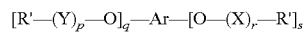

Ar is the aromatic portion of a diphenol;
X and Y are independently selected from:
—$CH_2COO$— (glycolic acid moiety);
—$CH(CH_3)COO$— (lactic acid moiety);
—$CH_2CH_2OCH_2COO$— (dioxanone moiety);
—$CH_2CH_2CH_2CH_2CH_2COO$— (caprolactone moiety);
—$(CH_2)_yCOO$— where y is independently selected from 2, 3, 4, 6, 7, 8, 9, 10, 11, 12, 13, 14, 15, 16, 17, 18, 19, 20, 21, 22, 23, and 24; and,
—$(CH_2CH_2O)_zCH_2COO$— where z is independently selected from 2, 3, 4, 5, 6, 7, 8, 9, 10, 11, 12, 13, 14, 15, 16, 17, 18, 19, 20, 21, 22, 23, and 24;
provided that the groups represented by [R'—$(Y)_p$—O]$_q$— and —[O—$(X)_r$—R]$_s$ are different from one another;
R' is selected from H, benzyl, and $C_{1-6}$ alkyl;
p is selected from 1, 2, 3, 4, 5, and 6;
q is selected from 1, 2, and 3.
r is selected from 1, 2, 3, 4, 5, and 6; and,
s is selected from 1, 2, and 3.

The unsymmetrical aromatic ether diacids of the present invention also include diesters when R' is other than H (as described above).

The group represented by X and Y is attached via their respective carbon terminus to the oxygen group of the diphenolic residue.

The rate of hydrolysis of the unsymmetrical aromatic ether diacids will depend upon a number of factors, including the functionalization species used and the number of functionalization species present on the diphenol (e.g., 2-6). Glycolic acid modified unsymmetrical aromatic ether diacids should hydrolyze faster than dioxanone modifies ones, where as lactic acid and caprolactone modified unsymmetrical aromatic ether diacids should take much longer to hydrolyze than glycolic acid and dioxanone modified unsymmetrical aromatic ether diacids. Furthermore, it is expected that the rate of hydrolysis will increase with the increase in the value of p and q. Thus, the desired time range may be obtained by altering the number and type of functionalization species used to functionalize the diphenol.

The present invention also provides novel unsymmetrical aromatic ether diacids of formula I, wherein:
y is independently selected from 2, 3, and 4;
z is independently selected from 2, 3, and 4;
p is selected from 1, 2, and 3;
q is selected from 1, 2, and 3;
r is selected from 1, 2, and 3; and,
s is selected from 1, 2, and 3.

The present invention also provides novel unsymmetrical aromatic ether diacids of formula I, wherein:
X and Y are independently selected from:
—$CH_2COO$—;
—$CH(CH_3)COO$—;
—$CH_2CH_2OCH_2COO$—; and,
—$CH_2CH_2CH_2CH_2CH_2COO$—;
p is selected from 1 and 2;
q is selected from 1 and 2;
r is selected from 1 and 2; and,
s is selected from 1 and 2.

The present invention also provides unsymmetrical aromatic ether diacids selected from:
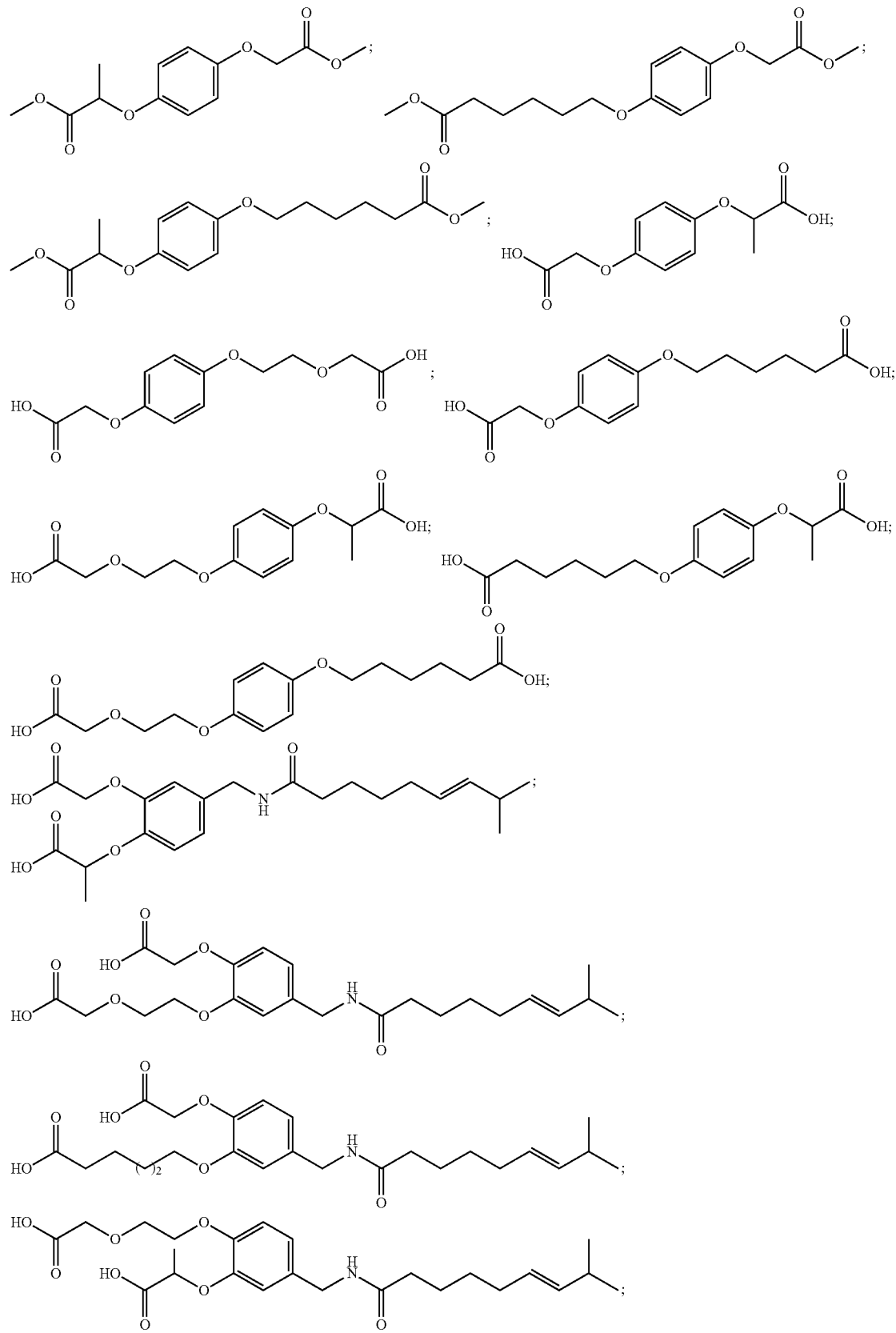

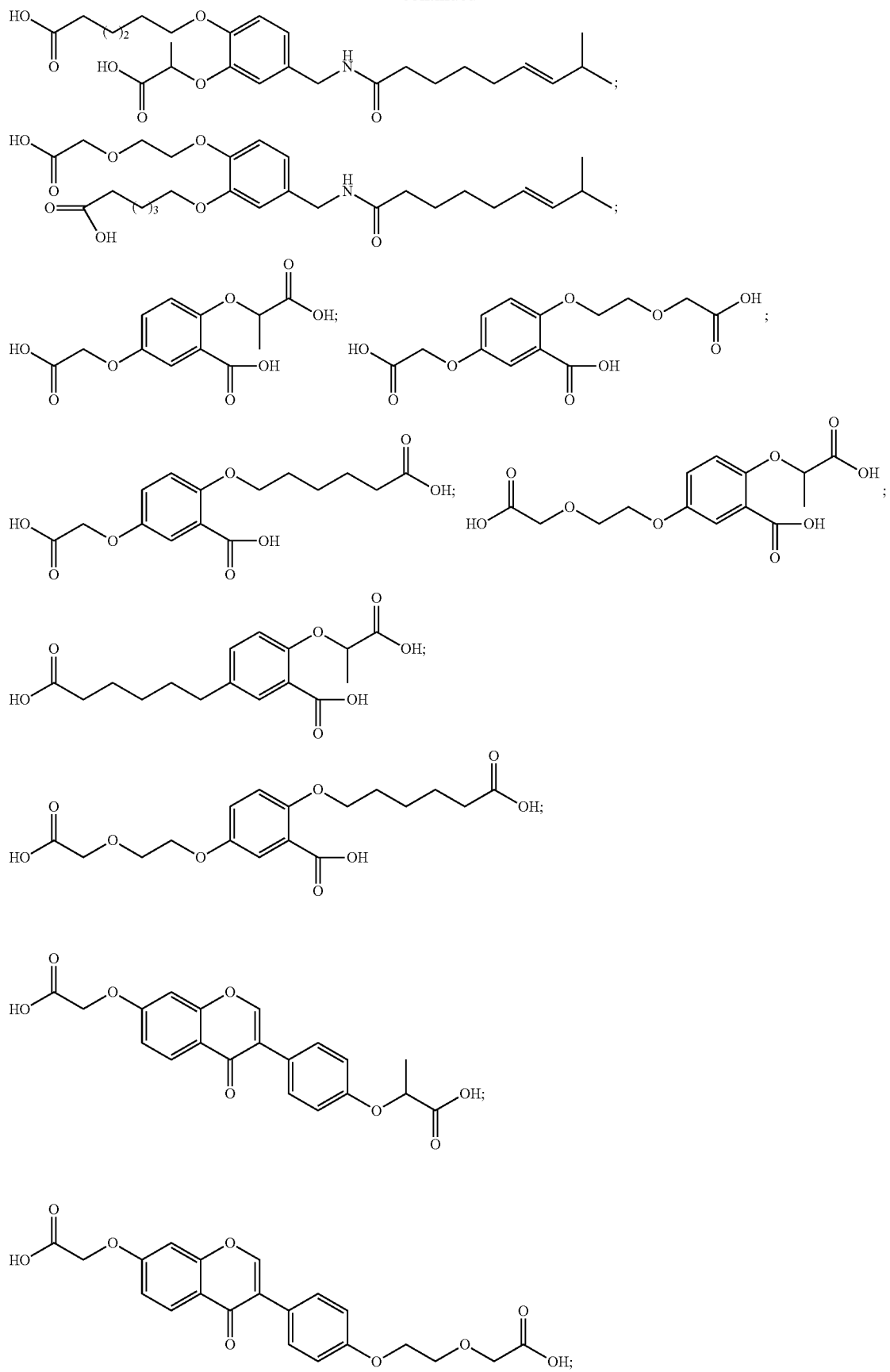

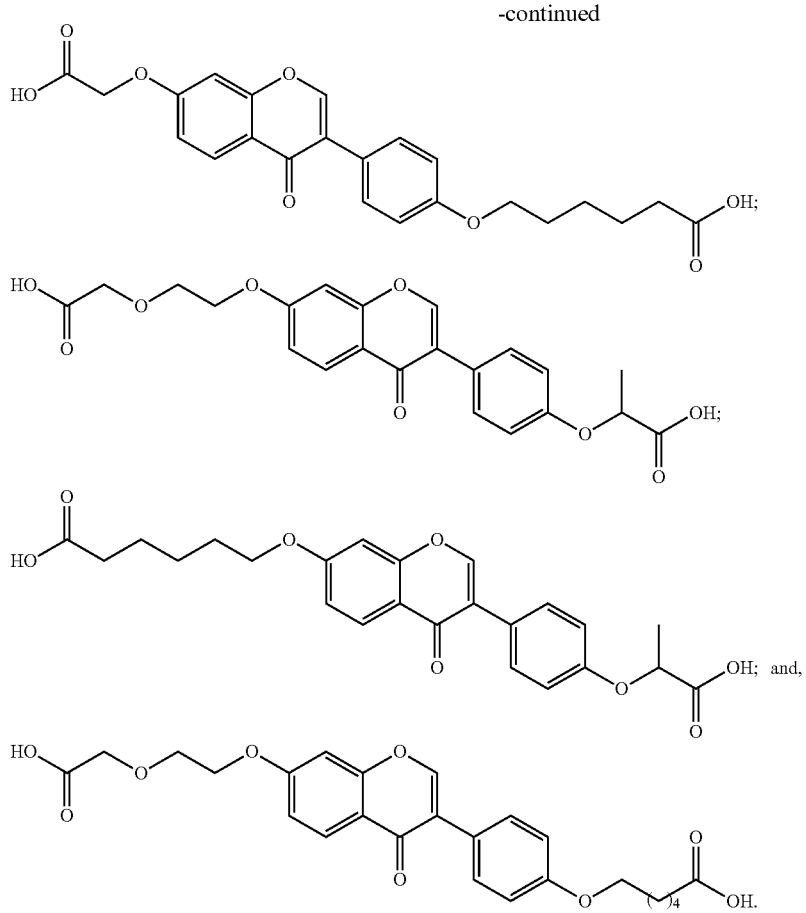

Examples of starting aromatic diols (or polyols) expected to be useful in the present invention include dihydroxyphenyls (e.g., resorcinol, catechol, and hydroquinone), tri-hydroxy-phenyls, naphthols (e.g., dihydroxynaphthyl, tri-hydroxynaphthyl, and tetra-hydroxynapthyl), hydroxybenzoic acids (e.g., dihydroxybenzoic acid), as well as other aromatics having at least two hydroxyl substituents (e.g., indoles, coumarins, acetophenones, benzophenones, flavonoids, drugs containing diphenol (at least two hydroxyl) groups and, natural products containing diphenol (at least two hydroxyl groups). Compounds containing at least two hydroxyl groups, one or more being protected hydroxyl groups (e.g., methoxy, ethoxy, and acetoxy) are also included.

Examples of naturally occurring phenolics include the following compounds and their derivatives: cinnamic acids (e.g., caffeic acid, chlorogenic acid, and ferulic acid), capsaicin, coumarins (e.g., isopimpinellin), alkaloids, catechins, chromones (including synthetic chromones), chalcones (including synthetic chromones), daidzein, 2,5-dihydroxybenzoic acid, flavonoids or bioflavonoids, isoflavones (e.g., daidzein, genistein, equol, glycitein, puerarin), resveratrol, sinapic acid, vanillic acid, and vanillin.

Examples of drugs containing phenolic groups include: adrenalone, alibendol, bamethan, benserazide, bevantolol, bifluranol, chlorotrianisene, cianidanol, cinepazide, cyclovalone, cynarine, denopamine, diacerein, dichlorophen, dienestrol, diethylstilbestrol, dilazep, dimestrol, dimoxyline, diosmin, dithranol, dobutamine, donepezil, dopamine, dopexamine, doxazosin, entacapone, epinephrine, etamivan, etamsylate, ethaverine, exifone, fenoldopam mesilate, fenoterol, fenoxedil, fenticlor, flopropione, floredil, fluorescein, folescutol, formoterol, gallopamil, gentistic acid, glaziovine, guajacol, hexachlorophene, hexestrol, hexobendine, hexoprenaline, hexylresorcinol, isoetarine, isoprenaline, itopride hydrochloride, khellin, levodopa, mebeverine, methoxamine, methyldopa, midodrine, mitoxantrone, morclofone, normolaxol, omeprazole, orciprenaline, oxypertine, oxyphenbutazone, oxyphenisatin acetate, papaverine, phenacaine, phenolphthalein, protokylol, raloxifene hydrochloride, reproterol, rimiterol, ritodrine, silibinin, sulmetozin, tamsulosin, terazosin, terbutaline, tetroxoprim, theodrenaline, tofisopam, tolcapone, tranilast, tretoquinol, trimazosin, trimetazidine, trimethobenzamide, trimethoprim, trimetozine, trimetrexate glucuronate, troxipide, verapamil, vesnarinone, vetrabutine.

Additional examples of phenolics (e.g., bioactive phenolics) include the following compounds and their derivatives: acacetin, albuterol, aloe-emodin, aloin, anthragallol, anthralin, anthrarufin, apigenin, apiin, apocynin, aspidinol, baptigenin, benzestrol, benzoresorcinol, catechin, chrysin, coniferyl alcohol, coumestrol, coumetarol, daphnetin, datiscetin, deoxyepinephrine, diosmetin, diresorcinol, dopa, dopamine, ellagic acid, embelin, Equol, eriodictyol, esculetin, eugenol, eupatorin, fisetin, fraxetin, fustin, galangin, gallacetophenone, gallic acid, gardenins, genistein, gentisyl alcohol, gossypol, guaiacol, homogentisic acid, homovanillic acid, hypericin, irigenin, isoproterenol, isoquercitrin, isothebaine, kaempferol, luteolin, mangostin, morin, mycophenolic acid, myricetin, naringenin, orcinol, osalmid, 3-pentadecylcatechol, phloretin, phloroglucinol, pyrogallol, quercetagetin, quercetin, resacetophenone, rhamnetin, rhein, sakuranetin, scopoletin, scutellarein.

Flavonoids, sometimes called bioflavonoids, are 3-ring phenolic compounds consisting of a double ring attached by a single bond to a third ring. Examples include flavonoids, flavanones, flavones, flavanols, anthocyanidins, proanthocyanidins, procyanidolic oligomers (PCO), catechins, biflavans, polyphenols, rutin, rutinosides, hydroxyethylrutosides (HER), hesperidin, quercetin, quercetrin, polyphenols, catechin, epicatechin, epicatechin gallate, epigallocatechin gallate, and leucoanthocyanins. Flavonoids include the water-soluble pigments, such as anthocyanins, that are found in cell vacuoles. Flavonols are colorless or yellow flavonoids found in leaves and many flowers.

A therapeutic dose of bioflavonoids is helpful for conditions related to Chronic Venous Insufficiency (CVI). Some examples are: thrombophlebitis, thrombosis, varicose veins, leg ulcers, spider veins, hemorrhoids, chronic nosebleeds, prolonged menstrual bleeding. Even eye problems like macular degeneration and diabetic retinopathy have been helped with bioflavonoids. Along with the anti-inflammatory effects, bioflavonoids can be very helpful for tendonitis, arthritis, rheumatoid arthritis, joint injury, fibromyalgia, cellulite, and gout. Bioflavonoids, specifically proanthcyanidins, are found in grape seed extract. The proanthcyanidins appear to enhance the activity of vitiamin C. The bioflavonoids in grape seed extract may also reduce the painful inflammation of swollen joints and prevent the oxidation of cholesterol in arteries that leads to plaque in the arterial walls.

Isoflavones exert a broad spectrum of biological activities. Besides antioxidant and estrogenic activities, isoflavones protect against several chronic diseases. Results of epidemiological studies indicate that consumption of soybean isoflavones lowers the incidence of breast, prostate, urinary tract and colon cancers. They also provide protection against coronary heart diseases and osteoporosis. Examples of isoflavones include are glycitein (isoflavone), daidzein, prunetin, biochanin A, orobol, santal, pratensein, formononetin, genistein, glycitein, and the glucosides, β-glycosides and other derivatives of the aforementioned isoflavones.

Resveratrol has been shown to lower the risk for coronary heart disease by inhibiting the plaque build-up or clogging of arteries by increasing the level of high density lipoproteins (HDLs) in the blood. Resveratrol also reduces blood platelet aggregation or clotting (thrombosis) within the blood vessels. Resveratrol belongs to the class of plant chemicals called phytoalexin. Plants use them as a defense mechanism in response to attacks by fungi and insects. One interesting phytoalexin called psolaren, having a chemical structure similar to coumarin, has been used in the treatment of certain cancers, including T-cell lymphomas in AIDS patients.

The capsaicins are amides of vanillylamine and $C_8$ and $C_{13}$ branched fatty acids. Examples of indications for capsaicins include peripheral neuropathic pain, post-herpetic neuralgia, trigeminal neuralgia, psoriasis, fibromyalgia, diabetic neuropathy, cluster headaches, earache, osteo- and rheumatoid arthritis, and as a pain reliever.

Sinapinic acid (sinapic acid) and its esterified forms are the predominant phenolic acid compounds found in rapeseed, contributing to its flavor and aroma. The sinapinic acid compounds have been shown to exhibit an anti-inflammatory action and have antimicrobial properties.

Tea polyphenols have been shown to block the nitrosation of amines by reducing nitrate to nitric acid or by forming C-nitroso compounds, thus blocking hepatotoxicity, lowering the risk of breast cancer metastasis. An example a component of green tea, epigallocatechin-3-gallate.

Further examples of phenolics useful in the present invention can be found in the following texts, which are incorporated by reference.
 a. Shahidi, Ferriodoon and Marian Naczk, *Phenolics in Food and Nutriceuticals*, Boca Raton, Fla.: CRC Press, 2003.
 b. Kleemann, A. et al, *Pharmaceutical Substances,* 4th Edition, Thieme (2000).
 c. *Phenolic Compounds in Food and Their Effects on Health II; Antioxidants and Cancer Prevention*, ACS Symposium Series No. 507, Washington, D.C.: ACS, 1992.
 d. *Food Phytochemicals for Cancer Prevention I*, ACS Symposium Series N. 546, Washington, D.C.: ACS, 1994.
 e. *ROMPP Encyclopedia Natural Products*, New York: Thieme, 2000.
 f. *The Merck Index,* 12$^{th}$ edition, Rahway, N.J.: Merck and Company, 1996.
 g. *A Single Source for Flavonoids and Coumarins* (2003), INDOFINE Chemical Company, Inc. 2004.

The present invention also provides a blend comprising one or more of the unsymmetrical aromatic diethers of the present invention with one or more species of diphenol compounds.

Polymers of the present unsymmetrical aromatic ether diacids are expected to have specific ranges over which they release the active diphenol moiety. One can blend polymers made from one or more unsymmetrical aromatic ether diacids and one or more species of diphenol moieties to obtain the release range desired for the specific application into the body of a mammalian, including a human or the environment. This release range varies with the species used for functionalization as well as the diphenol compound. The combinations or blends of these entities may comprise an amount of from 0.5% to 99.5% by weight of each species. The polymer blends can also include non-functionalized diphenol compounds.

In addition, the monomers of the present invention may be polymerized to form absorbable polymers that display excellent physical, chemical, and biological properties, which make them useful in medical applications. The polymers of the present invention are expected to form non-toxic degradation products by hydrolytic chain cleavage under physiological conditions. The novel polymers of the present invention are expected to have increased rate of degradation and bioresorption as well as controllable degradation profile in comparison to the currently available polymers.

For example, a diphenol, such as resorcinol, hydroquinone can be functionalized to form a reactive compound, which can be polymerized to form an absorbable polymer with a specific absorption profile. Similarly, each of the diphenols described above can be functionalized to form reactive monomers. The polymers derived from these monomers will have unique physical and biological properties with absorption profiles that are controllable.

Thus, the present invention provides novel polymers formed from unsymmetrical aromatic ether diacids of formula I:

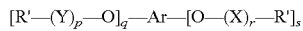   I

Ar is the aromatic portion of a diphenol;
X and Y are independently selected from:
 —CH$_2$COO— (glycolic acid moiety);
 —CH(CH$_3$)COO— (lactic acid moiety);
 —CH$_2$CH$_2$OCH$_2$COO— (dioxanone moiety);

—CH₂CH₂CH₂CH₂CH₂COO— (caprolactone moiety);

—(CH₂)ᵧCOO— where y is independently selected from 2, 3, 4, 6, 7, 8, 9, 10, 11, 12, 13, 14, 15, 16, 17, 18, 19, 20, 21, 22, 23, and 24; and, —(CH₂CH₂O)_zCH₂COO— where z is independently selected from 2, 3, 4, 5, 6, 7, 8, 9, 10, 11, 12, 13, 14, 15, 16, 17, 18, 19, 20, 21, 22, 23, and 24;

provided that the groups represented by [R'—(Y)_p—O]_q— and —[O—(X)_r—R]_s are different from one another;

R' is selected from H, benzyl, and C_{1-6} alkyl;

p is selected from 1, 2, 3, 4, 5, and 6;

q is selected from 1, 2, and 3.

r is selected from 1, 2, 3, 4, 5, and 6; and, s is selected from 1, 2, and 3.

As previously noted, the unsymmetrical aromatic ether diacids also include diesters when R' is other than H. When the unsymmetrical aromatic ether diacids are used as monomers to form polyesters, it may be desirable for R' to be other than H.

The group represented by X and Y are attached via their respective carbon terminus to the oxygen group of the diphenolic residue.

The unsymmetrical aromatic ether diacids of the present invention can be polymerized via conventional polymerization processes to form polyanhydrides or by using conventional polymerization processes and diol, triols, diamines, triamines, or a combination thereof based on the starting unsymmetrical aromatic ether diacids, including those processes that synthesize polymers traditionally considered hydrolytically stable and non-biodegradable. Carboxylic acids-based monomers can also be used in the polymerization when a polyanhydride is desired or when the unsymmetrical aromatic ether diacids contain an acid reactive functionality (e.g., a hydroxyl or amino group).

As noted above the present invention encompasses a variety of different copolymers, and optionally polymers. The polymers of the present invention include (a) polymers formed from one unsymmetrical aromatic ether diacid; (b) copolymers formed from at least one type of unsymmetrical aromatic ether diacid and a difunctional molecule (e.g., dialcohols, amino-alcohols, diamines, and dicarboxylic acids); (c) copolymers formed from more than one (e.g., 2, 3, or 4) type of unsymmetrical aromatic ether diacid (e.g., a blend of unsymmetrical aromatic ether diacids that is polymerized with themselves or with a difunctional molecule); and (d) copolymers formed from at least one of the polymers of (a)-(c) and at least one lactone monomer (e.g., glycolide, lactide, ε-caprolactone, trimethylene carbonate, and p-dioxanone). The absorption profile of the polymers of the present invention will depend upon a number of factors, including the functionalization species used and the number of functionalization species present on the unsymmetrical aromatic ether diacid (e.g., 2-6). Glycolic acid based polymers should hydrolyze faster than dioxanone based, where as lactic acid and caprolactone based polymers should take much longer to hydrolyze than glycolic acid and dioxanone based polymers. The desired time range may be obtained by altering the number and type of functionalization species as well as the number of different unsymmetrical aromatic ether diacids (e.g., a blend of two or more functionalized unsymmetrical aromatic ether diacids). The desired time range will also be affected by the moieties used for co-polymerization (e.g., difunctional compounds or lactone monomers).

The unsymmetrical aromatic ether diacid polymers can be used in various medical applications described herein or can be further polymerized with lactone monomers, such as glycolide, lactide, ε-caprolactone, trimethylene carbonate, and p-dioxanone, and the resulting absorbable unsymmetrical aromatic ether diacid/lactone copolymers can be used in the various medical applications described herein.

As noted above, more than one of the unsymmetrical aromatic ether diacids of the present invention can be blended and polymerized to form an unsymmetrical aromatic ether diacid copolymer. The functionalized diphenol copolymers can be used in various medical applications described herein or can be further polymerized with lactone monomers, such as glycolide, lactide, ε-caprolactone, trimethylene carbonate, and p-dioxanone, and the resulting absorbable polymers can also have the medical applications described herein.

As noted above, the unsymmetrical aromatic ether diacids of the present invention can be polymerized with difunctional molecules (e.g., dialcohols, amino-alcohols, diamines, and dicarboxylic acids) to form absorbable polymers, including but not limited to polyesters, polyester amides, polyamides, and polyanhydrides by simple polycondensation reactions. The unsymmetrical aromatic ether diacid/difunctional molecule polymers can be used in various medical applications or can be further polymerized with lactone monomers, such as glycolide, lactide, ε-caprolactone, trimethylene carbonate, and p-dioxanone, and the resulting absorbable polymers potential have the medical applications described above.

In another example of the present invention, the unsymmetrical aromatic ether diacids compounds of the present invention can be used in the preparation of polyanhydrides by reacting with dicarboxylic acid compounds. Dicarboxylic acids useful in the present invention have the following structure:

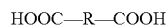

HOOC—R—COOH wherein R is selected from saturated and unsaturated, substituted and unsubstituted alkyl, aryl and alkylaryl groups having from 1, 2, 3, 4, 5, 6, 7, 8, 9, 10, 11, 12, 13, 14, 15, 16, 17, and 18 carbon atoms In another example of the present invention, the unsymmetrical aromatic ether diacids of the present invention can be used in the preparation of polyesters by reacting with the dialcohol (i.e., diol) compounds. Dialcohols useful in the present invention have the following structure:

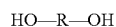

HO—R—OH wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms. Alternatively, polyalkylene oxides have weight average molecular weights from about 500-5,000 can be used as a diol (i.e., a polydiol). Suitable diols or polydiols for use in the present invention are diol or diol repeating units with up to 8 carbon atoms. Examples of suitable diols include 1,2-ethanediol (ethylene glycol); 1,2-propanediol (propylene glycol); 1,3-propanediol; 1,4-butanediol; 1,5-pentanediol; 1,3-cyclopentanediol; 1,6-hexanediol; 1,4-cyclohexanediol; 1,8-octanediol; and, combinations thereof. Examples of polydiols include polyethylene glycol and polypropylene glycol with weight average molecular weights of 500-5000.

In another example of the present invention, the unsymmetrical aromatic ether diacids of the present invention can be used in the preparation of polyesteramides by reacting with the amino-alcohol compounds. Amino-alcohols useful in the present invention have the following structure:

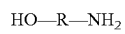

HO—R—NH₂ wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms.

In another example of the present invention, the unsymmetrical aromatic ether diacids of the present invention can be used in the preparation of polyamides by reacting with the diamine compounds. Diamines useful in the present invention have the following structure:

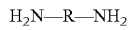

wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms. Alternatively, polyalkylene oxides that are diamines with weight average molecular weights from about 500-5,000 can be used.

The unsymmetrical aromatic ether diacids of the present invention having more than two reactive groups (e.g., 3) are expected to be useful in the preparation of cross linked hydrogels.

Examples of polymers of the present invention have weight-average molecular weights above about 20,000 daltons or above about 100,000 daltons, calculated from gel permeation chromatography (GPC) relative to polystyrene standards in tetrahydrofuran (THF) without further correction. Low-molecular weight polymers or oligomers as used herein means a polymer having a number average molecular weight of about 500-20,000 or 500-10,000.

The polymers of the present invention should be able to be processed by known methods commonly employed in the field of synthetic polymers to provide a variety of useful articles with valuable physical and chemical properties. The useful articles can be shaped by conventional polymer-forming techniques such as extrusion, compression molding, injection molding, solvent casting, and wet spinning. Shaped articles prepared from the polymers are expected to be useful as degradable devices for medical implant applications.

The present invention also relates to a composition, comprising: at least two (e.g., 2, 3, 4, or 5) functional unsymmetrical aromatic ether diacids of the present invention.

The present invention also relates to a composition, comprising: at least one unsymmetrical aromatic ether diacid, wherein the composition is suitable for use as at least one of the following: (a) a solvent for drugs; (b) a nutritional compound; (c) a cosmetic: and, (d) a pharmaceutical. Each of the compositions may further comprise an additional component suitable for such composition. For example, when the composition is suitable for use as a cosmetic it may further comprise: one or more cosmetic ingredients. Also, when the composition is suitable for use as a pharmaceutical it may further comprise: one or more pharmaceutically acceptable excipients. In addition, each of the compositions may comprise an unsymmetrical aromatic ether diacid derived from a diphenol having a property useful to that type of composition. For example, the starting diphenol may be (a) a nutritional supplement or a food intermediary; (b) an anticancer agent; (c) an antimicrobial agent; (d) an anti-inflammatory agent; (e) a pain-reducer; and, (f) an antioxidant agent. Also, the compositions may further comprise one of agents (a)-(f).

The compositions of the present invention may be suitable for administration via a route selected from oral, enteral, parenteral, topical, transdermal, ocular, vitreal, rectal, nasal, pulmonary, and vaginal.

The implantable medical devices of the present invention comprise: at least one absorbable polymer of the present invention. For example, a polymer of the present invention can be combined with a quantity of a biologically or pharmaceutically active compound sufficient to be therapeutically effective as a site-specific or systemic drug delivery system (see Gutowska et al., J. Biomater. Res., 29, 811-21 (1995) and Hoffman, J. Controlled Release, 6, 297-305 (1987)). Another example of the present invention is a method for site-specific or systemic drug delivery by implanting in the body of a patient in need thereof an implantable drug delivery device comprising a therapeutically effective amount of a biologically or a physiologically active compound in combination with at least one absorbable polymer of the present invention.

In another example, at least one polymer of the present invention is formed into a porous device (see Mikos et al., Biomaterials, 14, 323-329 (1993) or Schugens et al., J. Biomed. Mater. Res., 30, 449-462 (1996)) to allow for the attachment and growth of cells (see Bulletin of the Material Research Society, Special Issue on Tissue Engineering (Guest Editor: Joachim Kohn), 21(11), 22-26 (1996)). Thus, the present invention provides a tissue scaffold comprising a porous structure for the attachment and proliferation of cells either in vitro or in vivo formed from at least one absorbable polymer of the present invention The present invention also relates to an article (e.g., an implantable medical device), comprising: a metal or polymeric substrate having thereon a coating, wherein the coating, comprises: at least one polymer of the present invention.

The present invention also relates to a molded article prepared from at least one polymer of the present invention.

The present invention also relates to a controlled drug delivery system, comprising: at least one polymer of the present invention physically admixed with a biologically or pharmacologically active agent. For example, the controlled drug delivery system can comprise: a biologically or pharmacologically active agent coated with at least one polymer of the present invention.

The present invention also relates to a controlled drug delivery system, comprising: a biologically or pharmacologically active agent physically embedded or dispersed into a polymeric matrix formed from at least one polymer of the present invention.

The present invention also relates to a tissue scaffold having a porous structure for the attachment and proliferation of cells, either in vitro or in vivo, formed from one least one polymer of the present invention.

The present invention also relates to a composition, comprising: at least one polymer of the present invention, which has been further polymerized with at least one lactone monomer selected from: glycolide, lactide, p-dioxanone, trimethylene carbonate, and caprolactone.

The present invention also relates to an implantable biomedical device, comprising: at least one polymer that has been further polymerized with at least one lactone monomer.

The present invention also relates to a biodegradable chewing gum composition, comprising: an effective amount of at least one polymer that has been further polymerized with at least on lactone monomer.

The present invention also relates to an article (e.g., an implantable medical device), comprising: a metal or polymeric substrate and having thereon a coating, wherein said coating comprises at least one polymer that has been further polymerized with at least one lactone monomer.

The present invention also relates to a molded article prepared from at least one polymer that has been further polymerized with at least one lactone monomer.

The present invention also relates to a monofilament or multifilament prepared from at least one polymer that has been further polymerized with at least one lactone monomer.

The present invention also relates to a controlled drug delivery system, comprising: at least one polymer that has been further polymerized with at least one lactone monomer, which has been physically admixed with a biologically or pharmacologically active agent.

The present invention also relates to a controlled drug delivery system, comprising: a biologically or pharmacologically active agent physically embedded or dispersed into a polymeric matrix formed from at least one polymer that has been further polymerized with at least one lactone monomer.

The present invention also relates to a tissue scaffold having a porous structure for the attachment and proliferation of cells, either in vitro or in vivo, formed from at least one polymer that has been further polymerized with at least one lactone monomer.

The present invention also relates to low molecular weight polymers or oligomers of the unsymmetrical aromatic ether diacids of the present invention, which have been further reacted with excess diol to form hydroxy-terminated unsymmetrical aromatic ether diacids (i.e., diols). These hydroxyl terminated compounds or diols can then be reacted with diol-reactive monomers (e.g., isocyanates, epoxides, and acrylates). The diol capped unsymmetrical aromatic ether diacids can be reacted with dicarboxylic acids to form polyesters, which are usually hydroxy terminated. These hydroxyl terminated oligomers can be further reacted to form isocyanates, epoxides and acrylates. Similarly the diol capped unsymmetrical aromatic ether diacids can be reacted with isocyanates to make urethanes.

The present invention also relates to polymers made from unsymmetrical aromatic ether diacids that have been sterilized by cobalt-60 radiation, electron beam radiation, and/or ethylene oxide.

"Bioabsorbable" or "absorbable" as used herein means that the material readily reacts or enzymatically degrades upon exposure to bodily tissue for a relatively short period of time, thereby experiencing a significant weight loss in that short period of time. Complete bioabsorption/absorption should take place within twelve months, although it may be complete within nine months or within six months. In this manner, the polymers of the present invention can be fabricated into medical and surgical devices, which are useful for a vast array of applications requiring complete absorption within a relatively short time period.

The biological properties of the bioabsorbable polymers of the present invention used to form a device or part thereof, as measured by its absorption rate and its breaking strength retention in vivo (BSR), can be varied to suit the needs of the particular application for which the fabricated medical device or component is intended. This can be conveniently accomplished by varying the ratio of components of the polymer chosen.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat the desired indication.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, s-pentyl, and n-hexyl.

Polymers of the present invention may be made in the form of random copolymers or block copolymers. A coupling agent may also be added to the polymers of the present invention. A coupling agent is a reagent that has a least two functional groups that are capable of covalently bonding to two different monomers. Examples of coupling agents include trifunctional or tetrafunctional polyols, oxycarboxylic acids, and polybasic carboxylic acids (or acid anhydrides thereof). Other coupling agents include the difunctional groups (e.g., diols, diacids, diamines, and hydroxy-acids) previously discussed. The addition of the coupling agents causes the branching of long chains, which can impart desirable properties in the molten state to the pre-polymer. Examples of polyfunctional coupling agents include trimethylolpropane, glycerin, pentaerythritol, malic acid, citric acid, tartaric acid, trimesic acid, propanetricarboxylic acid, cyclopentanetetracarboxylic anhydride, and combinations thereof.

A "pre-polymer" is a low-molecular weight polymer, as previously defined, that have reactive end groups (e.g., hydroxy groups) that can be further reactive with, for example, the lactone monomers.

The amount of coupling agent to be added before gelation occurs is a function of the type of coupling agent used and the polymerization conditions of the polymer or molecular weight of the pre-polymer to which it is added. Generally in the range of from about 0.1 to about 10 mole percent of a trifunctional or a tetrafunctional coupling agent may be added based on the moles of polymers present or anticipated from the synthesis.

The polymerization of a polyester of the present invention can be performed under melt polycondensation conditions in the presence of an organometallic catalyst at elevated temperatures. The organometallic catalyst can be a tin-based catalyst (e.g., stannous octanoate or dibutyltin oxide). The catalyst can be present in the mixture at a mole ratio of diol, dicarboxylic acid, and optionally lactone monomer to catalyst will be in the range of from about 15,000/1 to 80,000/1. The reaction can be performed at a temperature not less than about 120° C. under reduced pressure. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and the glass transition temperature and softening temperature of the polymer. Desired reaction conditions of temperature, time and pressure can be readily determined by assessing these and other factors. Generally, the reaction mixture will be maintained at about 220° C. The polymerization reaction can be allowed to proceed at this temperature until the desired molecular weight and percent conversion is achieved for the copolymer, which will typically take about 15 minutes to 24 hours. Increasing the reaction temperature generally decreases the reaction time needed to achieve a particular molecular weight.

Polymerization conditions for the preparation of other types of polymers of the present invention (e.g., polyamides and polyurethanes) are described in the literature. Those skilled in the art will recognize that the polymers described herein can be made from known procedures.

Copolymers of the absorbable polymers of the present invention can be prepared by preparing a pre-polymer under melt polycondensation conditions, then adding at least one lactone monomer or lactone pre-polymer. The mixture could then be subjected to the desired conditions of temperature and time to copolymerize the pre-polymer with the lactone monomers.

A lactone pre-polymer is a pre-polymer formed by ring opening polymerization with a known initiator (e.g., ethylene glycol, diethylene glycol, glycerol, or other diols or triols).

The molecular weight of the pre-polymer as well as its composition can be varied depending on the desired characteristic, which the pre-polymer is to impart to the copolymer. For example, the pre-polymers of the present invention, from which the copolymer is prepared, generally have a molecular weight that provides an inherent viscosity between about 0.2 to about 2.0 deciliters per gram (dl/g) as measured in a 0.1 g/dl solution of hexafluoroisopropanol at 25° C. Those skilled in the art will recognize that the pre-polymers described herein can also be made from mixtures of more than one diol or dicarboxylic acid.

One of the beneficial properties of the polyesters of the present invention is that the ester linkages are hydrolytically unstable, and therefore the polymer is bioabsorbable because it readily breaks down into small segments when exposed to moist bodily tissue. In this regard, while it is envisioned that co-reactants could be incorporated into the reaction mixture of the dicarboxylic acid and the diol for the formation of the polyester pre-polymer, it is preferable that the reaction mixture does not contain a concentration of any co-reactant which would render the subsequently prepared polymer nonabsorbable. The reaction mixture can be substantially free of any such co-reactants if the presence thereof results in a nonabsorbable polymer.

The polymers of the present invention can be melt processed by numerous methods to prepare a vast array of useful devices. These polymers can be injection or compression molded to make implantable medical and surgical devices, especially wound closure devices.

Alternatively, the polymers can be extruded to prepare fibers. The filaments thus produced may be fabricated into sutures or ligatures, attached to surgical needles, packaged, and sterilized by known techniques. The polymers of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Examples include tubes, including branched tubes, for artery, vein, or intestinal repair, nerve splicing, tendon splicing, sheets for typing up and supporting damaged surface abrasions, particularly major abrasions, or areas where the skin and underlying tissues are damaged or surgically removed.

Additionally, the polymers can be molded to form films which, when sterilized, are useful as adhesion prevention barriers. Another alternative processing technique for the polymers of the present invention includes solvent casting, particularly for those applications where a drug delivery matrix is desired.

The polymers of the present invention can be used to coat a surface of a surgical article to enhance the lubricity of the coated surface. The polymer may be applied as a coating using conventional techniques. For example, the polymer may be solubilized in a dilute solution of a volatile organic solvent (e.g. acetone, methanol, ethyl acetate, or toluene), and then the article can be immersed in the solution to coat its surface. Once the surface is coated, the surgical article can be removed from the solution where it can be dried at an elevated temperature until the solvent and any residual reactants are removed.

For coating applications, the polymer should exhibit an inherent viscosity, as measured in a 0.1 gram per deciliter (g/dl) of hexafluoroisopropanol (HFIP), between about 0.05-2.0 dl/g or about 0.10-0.80 dl/g. If the inherent viscosity were less than about 0.05 dl/g, then the polymer may not have the integrity necessary for the preparation of films or coatings for the surfaces of various surgical and medical articles. On the other hand, it is possible to use polymers with an inherent viscosity greater than about 2.0 dl/g, though it may be difficult to do so.

Although numerous surgical articles (including but not limited to endoscopic instruments) can be coated with the polymer of the present invention to improve the surface properties of the article, specific surgical articles include surgical sutures, stents, and needles. For example the surgical article can be a suture, which can be attached to a needle. The suture can be a synthetic absorbable suture. These sutures are derived, for example, from homopolymers and copolymers of lactone monomers such as glycolide, lactide, ε-caprolactone, 1,4-dioxanone, and trimethylene carbonate. The suture can be a braided multifilament suture composed of polyglycolide or poly(glycolide-co-lactide).

The amount of coating polymer to be applied on the surface of a braided suture can be readily determined empirically, and will depend on the particular copolymer and suture chosen. Ideally, the amount of coating copolymer applied to the surface of the suture may range from about 0.5-30 percent of the weight of the coated suture or from about 1.0-20 weight percent, or from 1-5 percent by weight. If the amount of coating on the suture were greater than about 30 weight percent, then it may increase the risk that the coating may flake off when the suture is passed through tissue Sutures coated with the polymers of the present invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the polymer of the present invention.

When the article of the present invention is a metal stent, the amount of coating applied to the surface of the article is an amount which creates a layer with a thickness ranging, for example, between about 2-20 microns on the stent or about 4-8 microns. If the amount of coating on the stent were such that the thickness of the coating layer was greater than about 20 microns, or if the thickness was less than about 2 microns, then the desired performance of the stent as it is passed through tissue may not be achieved.

When the article of the present invention is a surgical needle, the amount of coating applied to the surface of the article is an amount which creates a layer with a thickness ranging, for example, between about 2-20 microns on the needle or about 4-8 microns. If the amount of coating on the needle were such that the thickness of the coating layer was greater than about 20 microns, or if the thickness was less than about 2 microns, then the desired performance of the needle as it is passed through tissue may not be achieved.

The polymers of the present invention can also be used as a pharmaceutical carrier in a drug delivery matrix. To form this matrix the polymer can be mixed with a therapeutic agent to form the matrix. There are a variety of different therapeutic agents, which can be used in conjunction with the polymers of the invention. In general, therapeutic agents which may be administered via the pharmaceutical compositions of the invention include, antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered in any suitable dosage form including orally, parenterally, subcutaneously as an implant, vaginally, or as a suppository. Matrix formulations containing the polymers of the present invention may be formulated by mixing one or more therapeutic agents with the polymer. The therapeutic agent, may be present as a liquid, a finely divided solid, or any other appropriate physical form. Typically, but optionally, the matrix will include one or more additives, e.g., nontoxic auxiliary substances such as diluents, carriers, excipients, or stabilizers. Other suitable additives may be formulated with the polymers of the present invention and pharmaceutically active agent. If water is to be used, then it can be useful to add it just before administration.

The amount of therapeutic agent will be dependent upon the particular drug employed and medical condition being treated. Typically, the amount of drug represents about 0.001%-70%, 0.001%-50%, or 0.001%-20% by weight of the matrix.

The quantity and type of polymer incorporated into a composition (e.g., parenterally delivered composition) will vary depending on the release profile desired and the amount of drug employed. The product may contain blends of polymers of the present invention to provide the desired release profile or consistency to a given formulation.

The polymers of the present invention, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (e.g., over 1-2,000 hours or 2-800 hours) of effective amounts (e.g., 0.0001 mg/kg/hour to 10 mg/kg/hour) of the drug. This dosage form can be administered as is necessary depending on the subject being treated, the severity of the affliction, and the judgment of the prescribing physician.

Individual formulations of drugs and polymers of the present invention may be tested in appropriate in vitro and in vivo models to achieve the desired drug release profiles. For example, a drug could be formulated with a polymer of the present invention and orally administered to an animal. The drug release profile could then be monitored by appropriate means such as, by taking blood samples at specific times and assaying the samples for drug concentration. Following this or similar procedures, those skilled in the art will be able to formulate a variety of formulations.

EXAMPLES

Example 1

(4-Benzyloxy-phenoxy)-acetic acid methyl ester

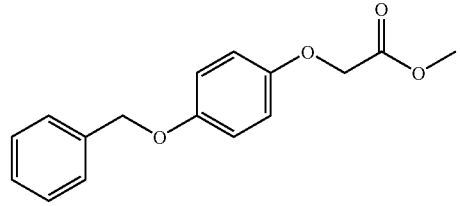

To a mixture of 4-benzyloxy phenol (40 grams, 200 mmol), anhydrous potassium carbonate (84 grams, 608 mmol), and sodium iodide (4 grams, 27 mmol) in anhydrous acetone (500 mL) was added methyl chloroacetate (24.3 grams, 224 mmol). The mixture was refluxed for 12 hours. Acetone was distilled off, and water (400 mL) was added. Crude 1 was filtered, dried, and recrystallized from a mixture of ethyl acetate:hexane (1:5) to give pure 1 (34 grams, 62.5%) as a white fluffy powder. M.p: 79-80° C. $^1$H NMR (CDCl$_3$) d 3.80 (s, 3H, ester), 4.52 (s, 2H$_2$OCH$_2$), 6.00 (s, 2H$_2$OCH$_2$), 6.82 (m, 5H,Ar), 7.35 (m, 4H,Ar).

Example 2

(4-Hydroxy-phenoxy)-acetic acid methyl ester

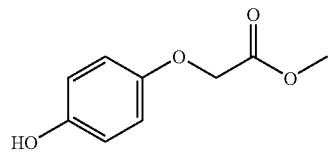

(4-Benzyloxy-phenoxy)-acetic acid methyl ester 1 (40 grams, 147 mmol) was dissolved in dry methanol (1000 mL) in a 3 liter round bottom flask. Pd/C (5%, 13 grams) was added, and the mixture stirred under an atmosphere of hydrogen for 10 hours. The catalyst was removed by filtration and the filtrate was distilled to give pure 2 (23 grams, 85.9%) as a white powder. M.p: 115-117° C. $^1$H NMR (CDCl$_3$+DMSO d$_6$) δ 3.72 (s, 3H, ester), 4.48 (s, 2H$_2$OCH$_2$), 6.64 (s, 4H,Ar), 8.48 (s, 1H$_2$OH).

Example 3

2-(4-Methoxycarbonylmethoxy-phenoxy)-propionic acid methyl ester

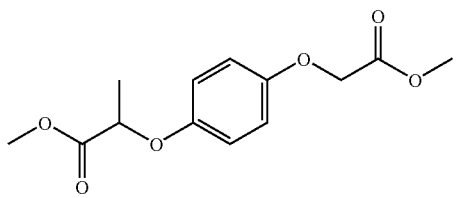

To a mixture of (4-hydroxy-phenoxy)-acetic acid methyl ester 2 (20 grams, 110 mmol), anhydrous K$_2$CO$_3$ (64 grams, 463 mmol), sodium iodide (16 grams, 107 mmol), and disodium phosphate (5 grams, 35.4 mmol) in anhydrous acetone (350 mL) was added methyl 2-chloro propionate (20 grams, 163 mmol). The mixture was refluxed for 30 hrs. Acetone was distilled off and water (300 mL) was added. Crude 3 was extracted into chloroform, dried over Na$_2$SO$_4$, distilled and purified by column chromatography on silica gel using benzene as eluent to give pure 3 (24 grams, 87.7%) as a syrup. $^1$HNMR (CDCl$_3$) δ 1.56 (d, 3H,CH$_3$), 3.70 (s, 3H, ester), 3.74 (s, 3H, ester), 4.48 (s, 2H$_2$OCH$_2$), 4.50 (q, 1H$_2$OCH), 6.74 (s, 4H,Ar).

Example 4

6-(4-Methoxycarbonylmethoxy-phenoxy)-hexanoic acid methyl ester

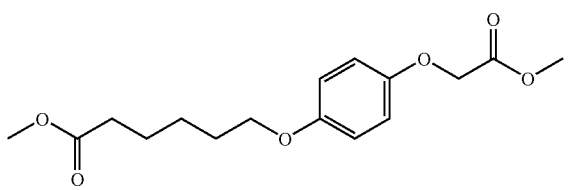

To a mixture of (4-hydroxy-phenoxy)-acetic acid methyl ester 2 (5 grams, 27.5 mmol), anhydrous K$_2$CO$_3$ (15 grams, 108.5 mmol), sodium iodide (5 grams, 33.3 mmol), and disodium phosphate (5 grams, 35.4 mmol) in anhydrous acetone (60 mL) was added methyl 2-bromo hexanoate (8 grams, 38.3 mol). The mixture was refluxed for 24 hrs. Acetone was distilled off and water (75 mL) added. Crude 6 was filtered, dried and recrystallized from ethyl acetate:hexane to give pure 6 (5 grams, 58.7%) as a white power. M.p: 61.5-63.5° C. $^1$HNMR (CDCl$_3$) d 1.54 (m, 2H, CH$_2$), 1.76 (m, 4H, CH$_2$), 2.34 (t, 2H, CH$_2$), 3.68 (s, 2H, Ester), 3.81 (s, 3H, Ester), 3.90 (t, 2H$_2$OCH$_2$), 4.38 (s, 2H$_2$OCH$_2$), 6.92 (s, 4H, Ar).

Example 5

6-(4-Benzyloxy-phenoxy)-hexanoic acid methyl ester

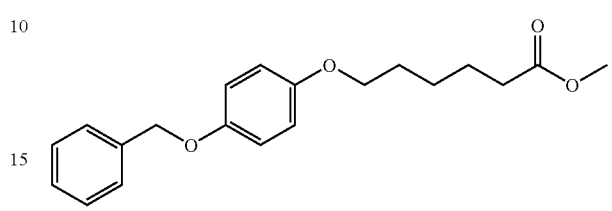

To a mixture of 4-benzyloxy phenol (100 grams, 490 mmol), anhydrous potassium carbonate (276 grams, 1.99 moles), sodium iodide (25 grams, 160 mmol), and disodium phosphate (25 grams, 170 mmol) in anhydrous acetone (1500 mL) was added methyl 6-bromohexanoate (135 grams, 640 mmol). The mixture was refluxed for 68 hrs. Acetone was distilled off and water (1500 mL) was added. Crude 5 was filtered, dried and recrystallized from a mixture of chloroform:hexane (1:6) to give pure 5 (120 grams, 73%) as a white power. M.p: 85-87° C. $^1$H NMR (CDCl$_3$) δ 1.52 (m, 2H, CH$_2$), 1.75 (m, 4H, CH$_2$), 2.38 (t, 2H, CH$_2$), 3.68 (s, 3H, ester), 3.94 (t, 2H$_2$OCH$_2$), 5.04 (s, 2H$_2$OCH$_2$), 6.82 (m, 4H, Ar), 7.38 (m, 5H, Ar).

Example 6

6-(4-Hydroxy-phenoxy)-hexanoic acid methyl ester

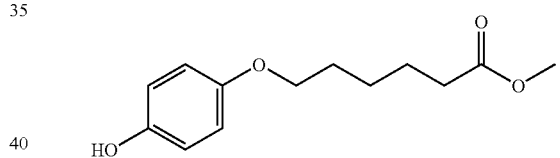

6-(4-Benzyloxy-phenoxy)-hexanoic acid methyl ester 5 (35 grams, 110 mmol) was dissolved in dry dimethyl formamide (350 mL) in a pressure vessel, and Pd/C (5%, 17.5 grams) added. The mixture was stirred under an atmosphere of hydrogen (3 Kg) for 6 hours. The catalyst was removed by filtration, and the filtrate was diluted with water (1500 mL). Crude 6, was filtered, washed with water, and dried to give pure 6 (22 grams, 87%) as a white power. M.p: 56-58.5° C. $^1$H NMR (CDCl$_3$) δ1.54 (m, 2H, CH$_2$), 1.78 (m, 4H, CH$_2$), 2.35 (t, 2H, CH$_2$), 3.68 (s, 3H, ester), 3.85 (t, 2H$_2$OCH$_2$), 4.90 (s, 1H$_2$OH), 6.70 (s, 4H, Ar).

Example 7

6-[4-(1-Methoxycarbonyl-ethoxy)-phenoxy]-hexanoic acid methyl ester

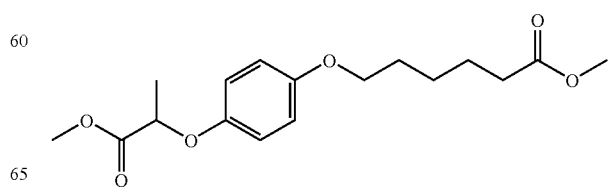

To a mixture of 6-(4-hydroxy-phenoxy)-hexanoic acid methyl ester 6 (28 grams, 120 mmol), anhydrous K$_2$CO$_3$ (64 grams, 460 mmol), sodium iodide (16.8 grams, 110 mmol), and disodium phosphate (16.8 grams, 120 mmol) in anhydrous acetone (700 mL) was added methyl 2-chloro propionate (18.6 grams, 150 mmol). The mixture was refluxed for 48 hrs. Acetone was distilled off and water (500 mL) was added. Crude 7 was extracted into chloroform, dried over Na$_2$SO$_4$, distilled, and purified by column chromatography on silica gel using benzene as eluent to give pure 7 (30 grams, 73%) as a Light Yellow liquid. $^1$HNMR (CDCl$_3$) δ 1.5 (m, 2H, CH$_2$), 1.61 (d, 3H, CH$_3$), 1.68 (m, 2H, CH$_2$), 1.76 (m, 2H, CH$_2$), 2.32 (t, 2H, CH$_2$), 3.66 (s, 3H, ester), 3.74 (s, 3H, ester), 3.86 (t, 2H$_2$OCH$_2$), 4.62 (q, 1H$_2$OCH), 6.78 (s, 4H, Ar).

Numerous modifications and variations of the present invention are possible in light of the above teachings. It is therefore to be understood that within the scope of the appended claims, the invention may be practiced otherwise that as specifically described herein.

What is claimed:

1. A compound of formula I or a pharmaceutically acceptable salt thereof:

[R'—(Y)$_p$—O]$_q$—Ar—[O—(X)$_r$—R']$_s$    I wherein:
Ar is the aromatic portion of a diphenol;
X and Y are independently selected from:
—CH$_2$COO—;
—CH(CH$_3$)COO—;
—CH$_2$CH$_2$OCH$_2$COO—;
—CH$_2$CH$_2$CH$_2$CH$_2$CH$_2$COO—;
—(CH$_2$)$_y$COO— where y is independently selected from 2-4 and 6-24; and
—(CH$_2$CH$_2$O)$_z$CH$_2$COO— where z is independently selected from 2-24;
provided that the groups represented by [R'—(Y)$_p$—O]$_q$— and —[O—(X)$_r$—R']$_s$ are different from one another;
R' is selected from H, benzyl, and C$_{1-6}$ alkyl;
p is selected from 1, 2, 3, 4, 5, and 6;
q is selected from 1, 2, and 3;
r is selected from 1, 2, 3, 4, 5, and 6; and
s is selected from 1, 2, and 3.

2. A compound according to claim 1 wherein:
Ar is an optionally substituted diphenolic residue selected from:

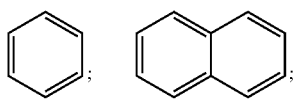

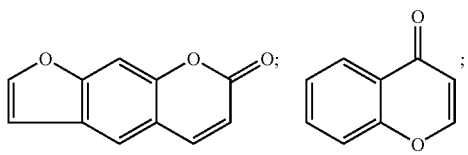

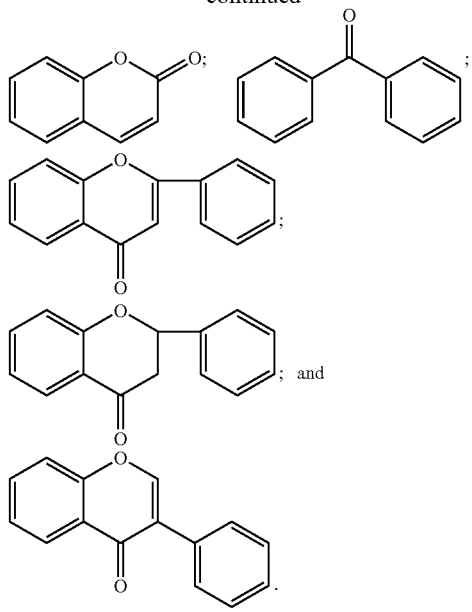

3. A compound according to claim 2, wherein
y is independently selected from 2, 3, and 4;
z is independently selected from 2, 3, and 4;
p is selected from 1, 2, and 3;
q is selected from 1, 2, and 3;
r is selected from 1, 2, and 3; and
s is selected from 1, 2, and 3.

4. A compound according to claim 2, wherein
X and Y are independently selected from:
—CH$_2$COO—;
—CH(CH$_3$)COO—;
—CH$_2$CH$_2$OCH$_2$COO—; and
—CH$_2$CH$_2$CH$_2$CH$_2$CH$_2$COO—;
p is selected from 1 and 2;
q is selected from 1 and 2;
r is selected from 1 and 2; and
s is selected from 1 and 2.

5. A compound according to claim 2, wherein Ar is an optionally substituted diphenolic residue selected from:

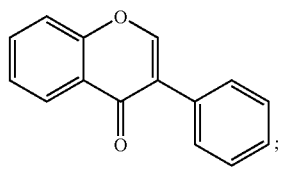

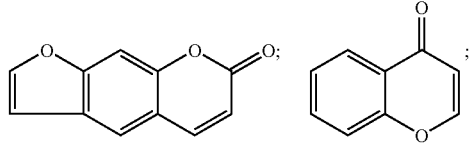

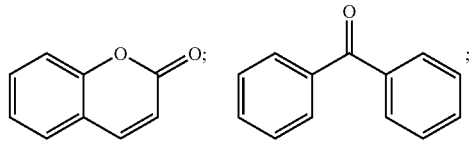

-continued

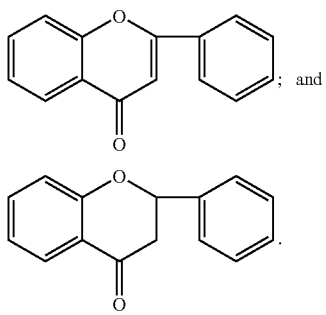; and

6. A compound according to claim 5, wherein Ar is an optionally substituted diphenolic residue selected from:

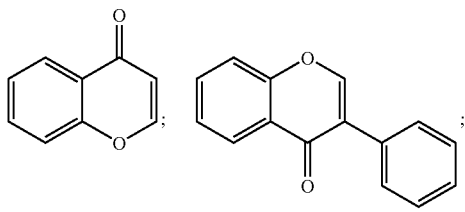; and

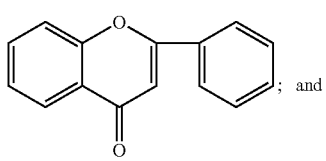.

7. A compound according to claim 6, wherein Ar is an optionally substituted diphenolic residue of formula:

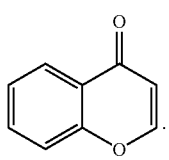.

8. A compound according to claim 6, wherein Ar is an optionally substituted diphenolic residue of formula:

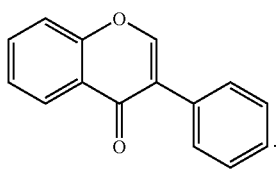.

9. A compound according to claim 8, Ar is a diphenolic residue of formula:

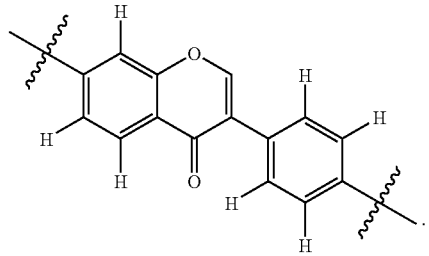.

10. A compound according to claim 6, wherein Ar is an optionally substituted diphenolic residue of formula:

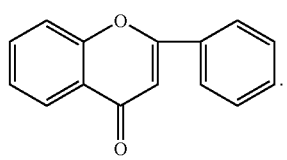.

11. A compound according to claim 6, wherein Ar is an optionally substituted diphenolic residue of formula:

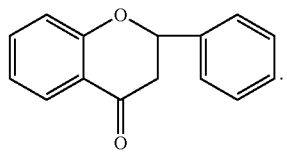.

12. A compound according to claim 5, wherein:

each Ar group is independently substituted with 1, 2, or 3 R groups, wherein:

R is independently selected from =O, O-glycosides, $-(CH_2)_{0-2}-OR^a$, $-(CH_2)_{0-2}-C_6H_5$, $-(CH_2)_{0-2}-CHO$, Cl, F, Br, I, $-(CH_2)_{0-2}-OC(O)-R^a$, $-(CH_2)_{0-2}-CO_2-R^a$, $-(C(CH_3))_{0-2}-CO_2-R^a$, $-(CH_2)_{0-2}-CO_2-(CH_2)_{1-2}-CO_2-R^a$, $-(C(CH_3))_{0-2}-CO_2-(CH_2)_{1-2}-CO_2-R^a$, $-(CH_2)_{0-2}-CO-R^a$, $-O(CH_2)_{0-2}-C_6H_5$, $-O(CH_2)_{1-2}-CO_2-R^a$, $-O(C(CH_3))_{1-2}-CO_2-R^a$, $-O(CH_2)_{1-2}-CO-R^a$, $-CO_2(CH_2)_{1-2}-CO_2-R^a$, $-CO_2(C(CH_3))_{1-2}-CO_2-R^a$, $-(CH_2)_{0-2}-NO_2$, $-(CH_2)_{0-2}-NR^aR^a$, $-(CH_2)_{0-2}-NR^aCOR^a$, $-(CH_2)_{0-2}-NR^aC(O)(CH_2)_{1-2}OR^a$, $-C_6H_5$, $-C_6H_5OR^a$, and $-C_6H_5-CH=CHCO_2R^a$; and, $R^a$ is independently selected from H and $C_{1-6}$ alkyl.

13. A compound according to claim 2, wherein the compound is selected from:
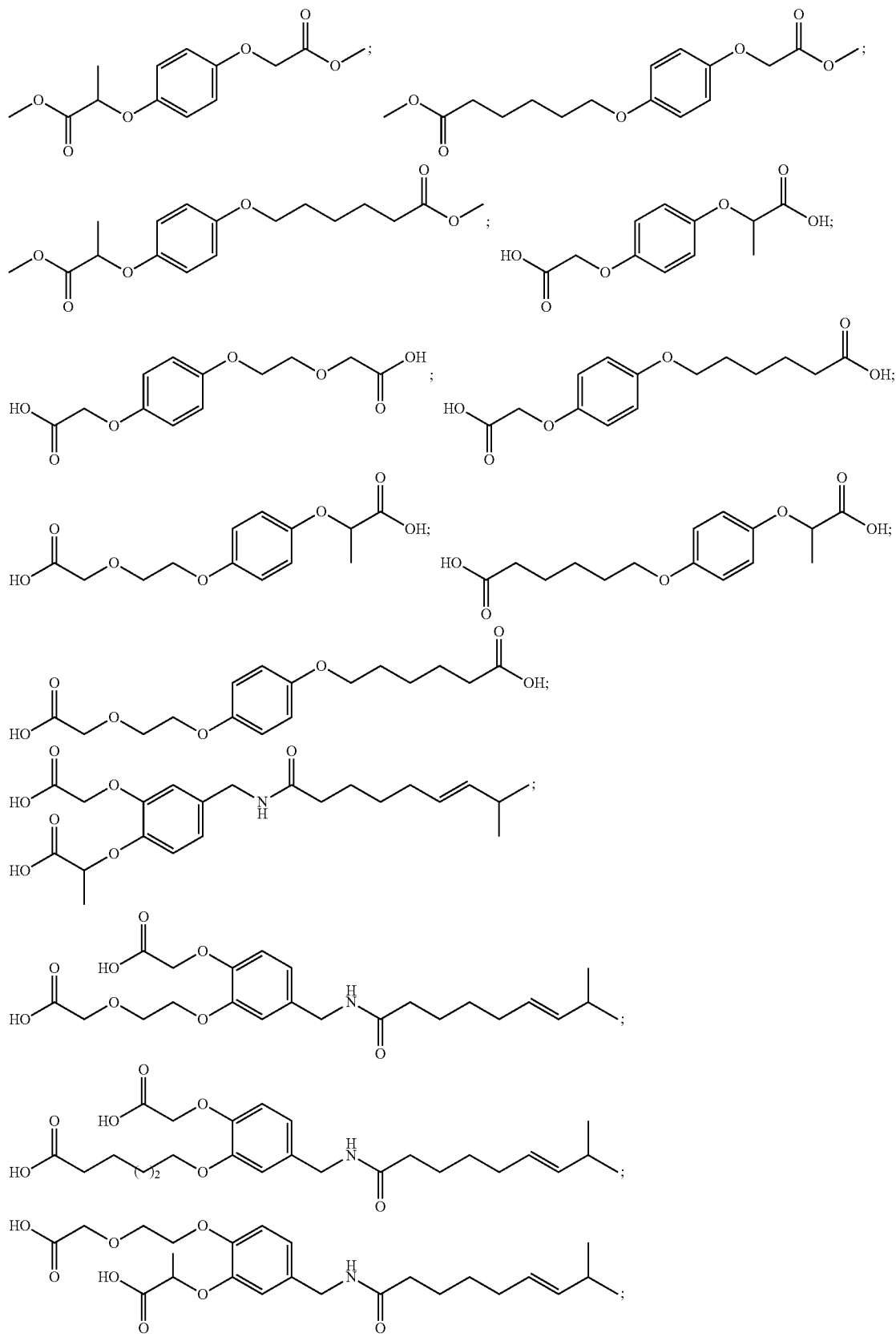

-continued
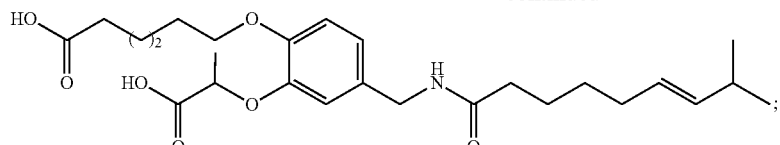
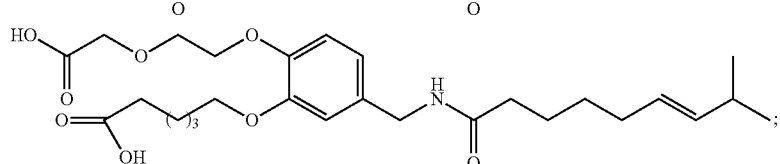
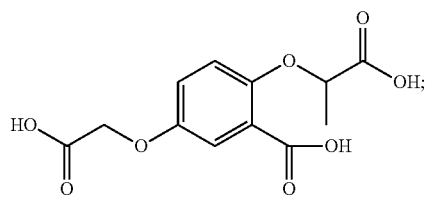
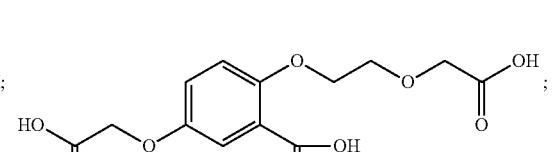
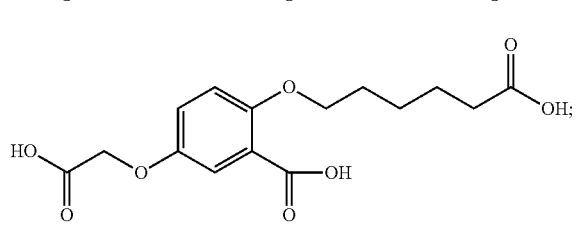
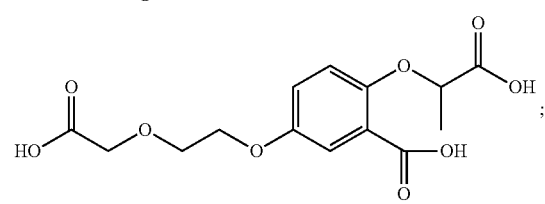
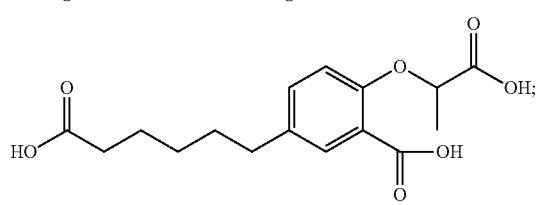
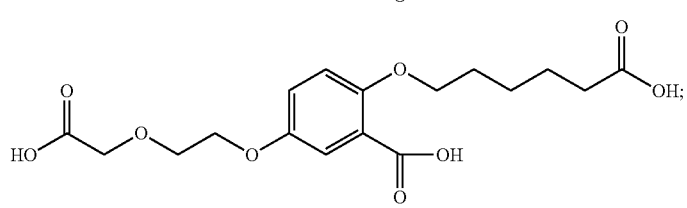
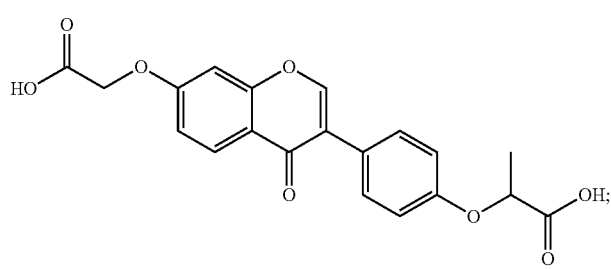
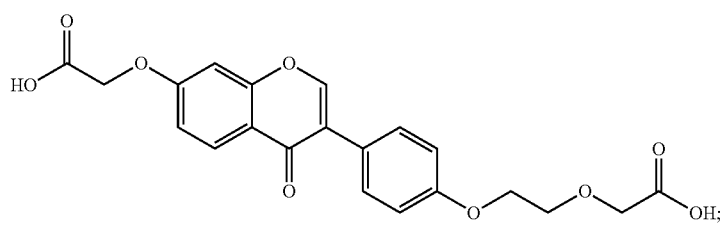

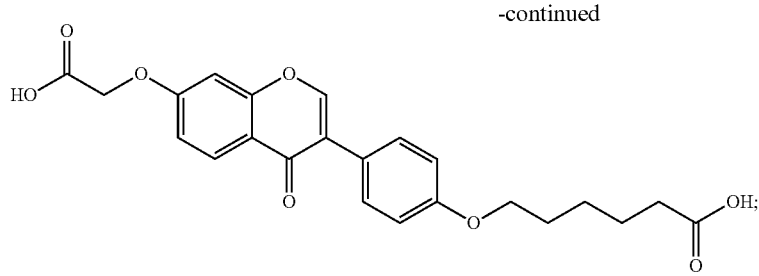
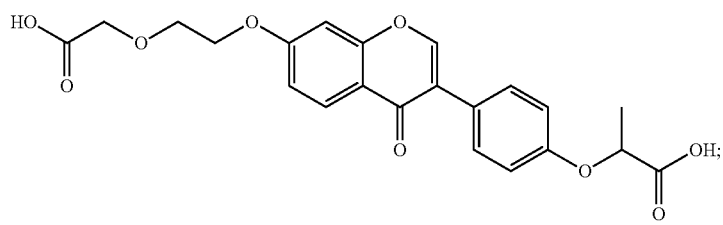
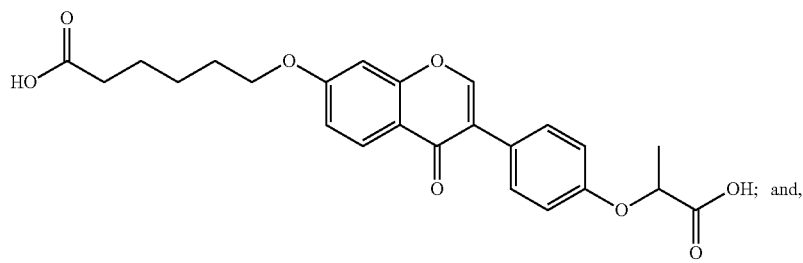
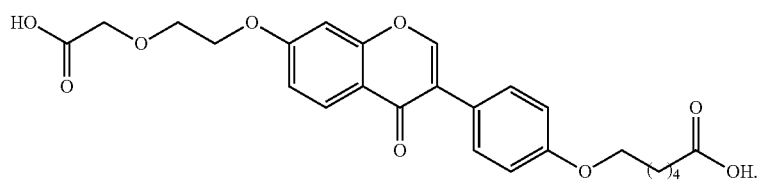
14. A compound according to claim 9, wherein the compound is selected from:
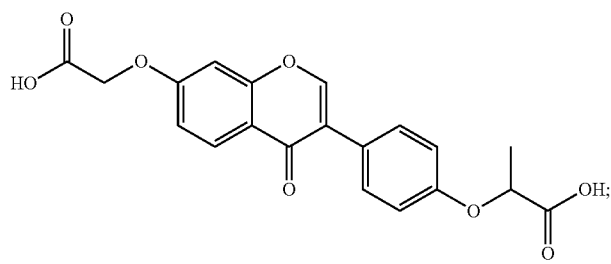
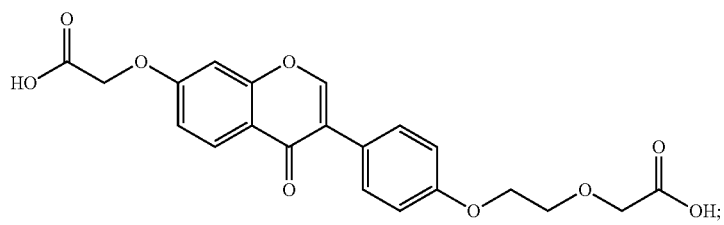

-continued

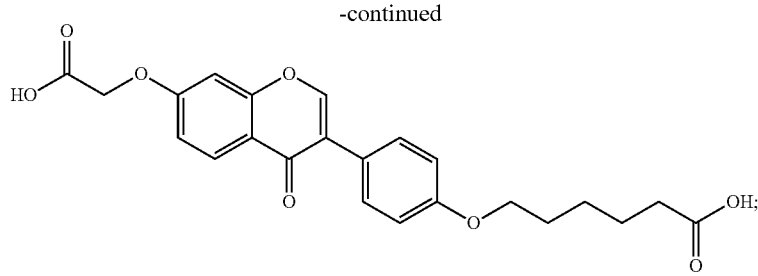

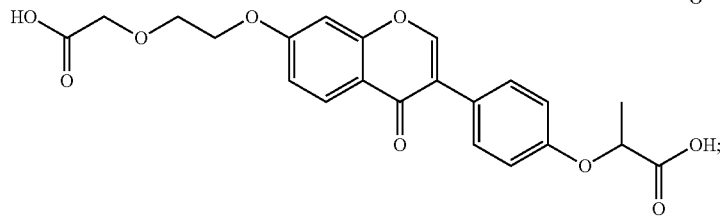

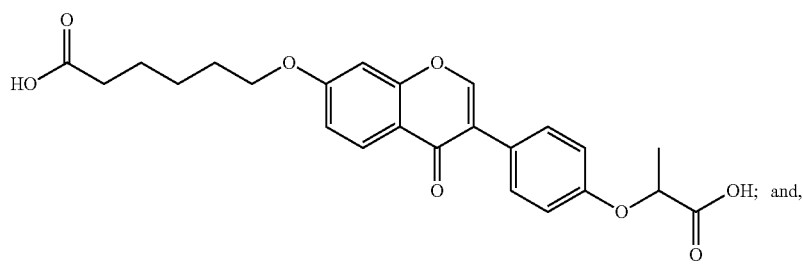

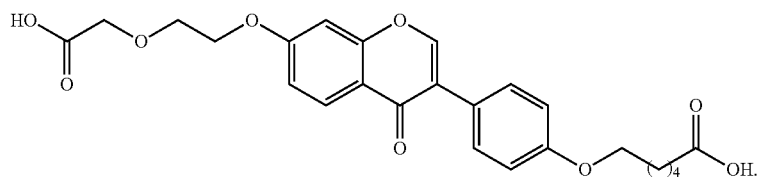

15. A composition, comprising: at least two different compounds according to claim 1.

16. A solvent for a drug, comprising: at least one compound according to claim 1.

17. A nutritional composition, comprising at least one compound according to claim 1.

18. The nutritional composition according to claim 17, wherein the diphenolic residue in the compound of formula I was derived from a compound that is a nutritional supplement or a food intermediary.

19. A cosmetic composition, comprising at least one compound according to claim 1 and a cosmetic ingredient.

20. A pharmaceutical composition, comprising at least one compound according to claim 1 and a pharmaceutically acceptable excipient.

21. The composition according to claim 20, wherein the composition is suitable for administration via a route selected from oral, enteral, parenteral, topical, transdermal, ocular, vitreal, rectal, nasal, pulmonary, and vaginal.

22. The composition according to claim 20, wherein the diphenolic residue in the compound of formula I was derived from a cancer preventing diphenol.

23. The composition according to claim 22, further comprising: an anti-cancer agent.

24. The composition according to claim 20, wherein the diphenolic residue in the compound of formula I was derived from a phenolic with antimicrobial properties.

25. The composition according to claim 24, further comprising: an antimicrobial agent.

26. The composition according to claim 20, wherein the diphenolic residue in the compound of formula I was derived from a phenolic with anti-inflammatory properties.

27. The composition according to claim 26, further comprising: anti-inflammatory agent.

28. The composition according to claim 20, wherein the diphenolic residue in the compound of formula I was derived from a phenolic with pain-reducing properties.

29. The composition according to claim 28, further comprising: a pain reducing agent.

30. The composition according to claim 20, wherein the diphenolic residue in the compound of formula I was derived from a phenolic with antioxidant properties.

31. The composition according to claim 30, further comprising: an antioxidant agent.

32. A compound according to claim 1, wherein Ar is a synthetic or naturally derived flavanoid diphenolic residue.

33. A compound according to claim 32, wherein the flavanoid is selected from:

flavonoids, flavanones, flavones, flavanols, anthocyanidins, proanthocyanidins, procyanidolic oligomers (PCO), catechins, biflavans, polyphenols, rutin, rutinosides, hydroxyethylrutosides (HER), hesperidin, quercetin, quercetrin, polyphenols, catechin, epicatechin, epicatechin gallate, epigallocatechin gallate, leucoanthocyanins, anthocyanins, and isoflavones; and glucosides or β-glycosides thereof.

34. A compound according to claim 33, wherein the isoflavone is selected from:
   glycitein, daidzein, prunetin, biochanin A, orobol, santal, pratensein, formononetin, genistein, and glycitein; and glucosides or β-glycosides thereof.

* * * * *